United States Patent [19]
Benson et al.

[11] Patent Number: 5,272,143
[45] Date of Patent: Dec. 21, 1993

[54] 6-OXOAZEPINOINDOLE COMPOUNDS, AND PHARMACEUTICAL COMPOSITIONS CONTAINING THEM

[75] Inventors: Werner Benson, Seelze OT Letter, Fed. Rep. of Germany; Karin van Charldorp, AK Hilversum, Netherlands; Peter C. Gregory, Hanover, Fed. Rep. of Germany; Klaus-Ullrich Wolf, Haenigsen, Fed. Rep. of Germany; Ulf Preuschoff, Uelzen, Fed. Rep. of Germany; Martin Tulp, GJ Muiderberg, Netherlands; Ton Hulkenberg, Bunschoten, Netherlands; Ineke van Wijngaarden, Oud-Turnhout, Belgium

[73] Assignee: Kali-Chemie Pharma GmbH, Hanover, Fed. Rep. of Germany

[21] Appl. No.: 922,527

[22] Filed: Jul. 31, 1992

[30] Foreign Application Priority Data

Jul. 31, 1991 [DE] Fed. Rep. of Germany ....... 4125292

[51] Int. Cl.$^5$ .................. C07D 487/04; A61K 31/55
[52] U.S. Cl. ..................................... 514/215; 540/520
[58] Field of Search ......................... 514/215; 540/520

[56] References Cited

U.S. PATENT DOCUMENTS 4,910,193  3/1990  Buchheit ........................... 514/216

OTHER PUBLICATIONS

Clark et al., J. Med. Chem., vol. 33, pp. 633–641 (1990).

Primary Examiner—John M. Ford
Attorney, Agent, or Firm—Evenson, McKeown, Edwards & Lenahan

[57] ABSTRACT

Pharmacologically active compounds corresponding to the general formula I

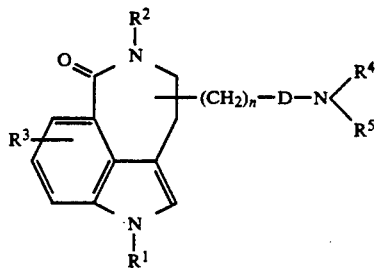

in which
- $R^1$ represents hydrogen, a lower alkyl or cycloalkyl-alkyl group or an optionally substituted phenyl-lower alkyl group,
- $R^2$ denotes hydrogen or a lower alkyl group optionally substituted in the α-position to the nitrogen atom by lower alkoxy,
- $R^3$ denotes hydrogen, lower alkyl, lower alkoxy, halogen or hydroxyl,
- n represents 1 or, if the —$(CH_2)_n$— chain is in the 4-position of the ring structure, also represents 2,
- $R^4$ denotes hydrogen, lower alkyl, cycloalkyl, cycloalkyl-lower alkyl or an optionally substituted phenyl-lower alkyl group, and
- $R^5$ denotes hydrogen, lower alkyl, cycloalkyl, cycloalkyl-lower alkyl or an optionally substituted phenyl-lower alkyl group, or
- $R^4$ and $R^5$, together with the nitrogen atom to which they are bonded, form a heterocycle and
- D represents a bond, or, if $R^4$ and $R^5$ do not denote hydrogen, also represents the —N=CH— group, and their physiologically acceptable acid addition salts are described, and also processes and intermediates for their preparation.

8 Claims, No Drawings

6-OXOAZEPINOINDOLE COMPOUNDS, AND PHARMACEUTICAL COMPOSITIONS CONTAINING THEM

BACKGROUND OF THE INVENTION

The present invention relates to novel 6-oxo-3,4,5,6-tetrahydro-1H-azepino[5,4,3-cd]indole derivatives and their salts carrying an optionally substituted aminoalkyl radical in the 3- or 4- position of the ring structure and to pharmaceutical preparations containing these compounds and processes and intermediates for the preparation of these compounds.

Japanese Patent Application No. 1,034,988 describes 6-oxotetrahydroazepinoindoles as intermediates for the preparation of diuretic tetrahydroazepinoindoles. Japanese Patent Application No. 57,144,286 discloses tetrahydroazepinoindoles having coronary vasodilatory properties.

SUMMARY OF THE INVENTION

It is the object of the present invention to provide new 6-oxo-3,4,5,6-tetrahydro-1H-azepino[5,4,3-cd]indole compounds having useful pharmacological properties.

This and other objects of the invention are achieved by providing compounds corresponding to the formula I

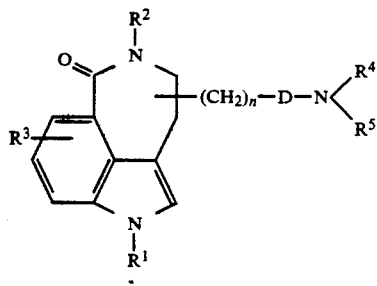

wherein $R^1$ represents hydrogen, a lower alkyl or cycloalkylalkyl group or a phenyl-lower alkyl group which can optionally be mono- or disubstituted in the phenyl ring by lower alkoxy, hydroxyl, halogen or lower alkyl, $R^2$ represents hydrogen or a lower alkyl group optionally substituted in the α-position to the nitrogen atom by lower alkoxy, $R^3$ denotes hydrogen, lower alkyl, lower alkoxy, halogen, or if $R^1$, $R^2$, $R^4$ and $R^5$ are free of lower alkoxy groups, $R^3$ may also be hydroxyl, n represents 1, or if the -(CH$_2$)$_n$— chain is in the 4-position of the ring structure, n may also represent 2;

$R^4$ denotes hydrogen, alkyl having 1 to 5 carbon atoms, cycloalkyl having 3 to 6 carbon atoms, cycloalkylalkyl having 4 to 9 carbon atoms or a phenyl-lower alkyl group optionally mono- or disubstituted in the phenyl ring by lower alkyl, lower alkoxy, hydroxyl or halogen, and $R^5$ denotes hydrogen, alkyl having 1 to 5 carbon atoms, cycloalkyl having 3 to 6 carbon atoms, cycloalkylalkyl having 4 to 9 carbon atoms or a phenyl-lower alkyl group optionally mono- or disubstituted in the phenyl ring by lower alkyl, lower alkoxy, hydroxyl or halogen, or $R^4$ and $R^5$, together with the nitrogen atom to which they are bonded, form a heterocycle corresponding to the formula

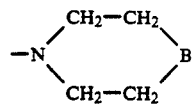

wherein B represents a bond, the methylene group, oxygen, or an imino group —NR$^6$—, in which R$^6$ denotes hydrogen, lower alkyl or phenyl or benzyl optionally substituted in the phenyl ring by lower alkyl, lower alkoxy, hydroxyl or halogen, and D represents a bond, or if $R^4$ and $R^5$ are other than hydrogen, D may also represent the —N=CH— group, and their physiologically acceptable acid addition salts.

It has been found that the novel 6-oxo-3,4,5,6-tetrahydro-1H-azepino[5,4,3-cd]indole derivatives which carry an optionally substituted aminomethyl or aminoethyl group in the 3- or 4-position of the ring structure have useful pharmacological properties and in particular exhibit an advantageous pharmacological activity in the gastrointestinal tract and are distinguished by a gastric motility-promoting action. The compounds additionally have serotonin-agonistic actions on 5-HT$_1$-like receptors, which are an index for properties favorably influencing migraine conditions. Due to their activities, the compounds according to the invention are suitable for the treatment of gastric motility disorders and for the treatment of migraine.

In accordance with further aspects of the invention, the object of the invention is also achieved in part by providing a process and intermediates as described hereinafter for preparing the compounds of the invention.

DETAILED DESCRIPTION OF PREFERRED EMBODIMENTS

The present invention therefore relates to novel compounds of the general formula I

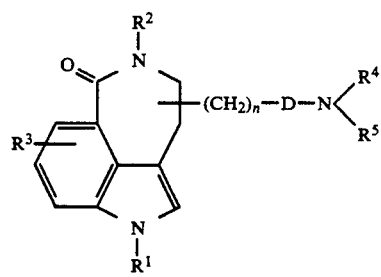

in which $R^1$ represents hydrogen, a lower alkyl or cycloalkylalkyl group or a phenyl-lower alkyl group which can optionally be mono- or disubstituted in the phenyl ring by lower alkoxy, hydroxyl, halogen or lower alkyl, $R^2$ represents hydrogen or a lower alkyl group optionally substituted in the α-position to the nitrogen atom by lower alkoxy, $R^3$ denotes hydrogen, lower alkyl, lower alkoxy, halogen or, if the substituents $R^1$, $R^2$, $R^4$ and/or $R^5$ do not contain any lower alkoxy groups, also denotes hydroxyl, n represents 1 or, if the —(CH$_2$)$_n$— chain is in the 4-position of the ring structure, also represents 2, $R^4$ denotes hydrogen, alkyl having 1 to 5 carbon atoms, cycloalkyl having 3 to 6 carbon atoms, cycloalkylalkyl having 4 to 9 carbon atoms or a phenyl-lower alkyl group optionally mono- or disubstituted in the phenyl ring by lower alkyl, lower alkoxy, hydroxyl or halogen, and $R^5$ denotes hydrogen, alkyl having 1 to 5 carbon atoms, cycloalkyl having 3 to 6 carbon atoms, cycloalkylalkyl having 4 to 9 carbon atoms or a phenyl-lower alkyl group optionally mono- or disubstituted in the phenyl ring by lower alkyl, lower alkoxy, hydroxyl or halogen, or $R^4$ and $R^5$, together with the nitrogen atom to which they are bonded, form a heterocycle of the general formula a

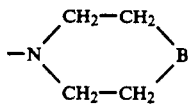

in which

B represents a bond, the methylene group, oxygen or an imino group —$NR^6$—, in which $R^6$ denotes hydrogen, lower alkyl or phenyl or benzyl optionally substituted in the phenyl ring by lower alkyl, lower alkoxy, hydroxyl or halogen, and D represents a bond or, if $R^4$ and $R^5$ do not denote hydrogen, also represents the —N=CH— group, and their physiologically acceptable acid addition salts.

If in the compounds of the formula I the substituents contain lower alkyl groups, these alkyl groups can be straight or branched and in particular contain 1 to 4, preferably 1 to 2, carbon atoms and preferably represent methyl. If the substituents denote halogen or contain halogen substituents, fluorine, chlorine or bromine, preferably chlorine, are suitable.

The substituent $R^1$ preferably represents hydrogen. If $R^1$ represents a lower alkyl group, this can be straight-chain, branched or cyclic and can preferably contain 1 to 4 carbon atoms and in particular represents methyl. If $R^1$ represents a phenyl-lower alkyl group, its alkylene chain can contain 1 to 4 carbon atoms. The phenyl ring can be unsubstituted or mono- or disubstituted by lower alkoxy, preferably methoxy, or alternatively by halogen, hydroxyl or lower alkyl. Cycloalkylalkyl radicals $R^1$ can contain cycloalkyl groups having 3 to 6 carbon atoms and an alkylene chain having 1 to 3 carbon atoms.

The substituent $R^2$ preferably represents hydrogen. If $R^2$ represents a lower alkyl group, this can contain 1 to 4, in particular 1 or 2, carbon atoms and is preferably substituted by lower alkoxy, in particular methoxy, and represents, for example, the methoxymethyl group.

The substituent in the azepine ring is preferably in the 3-position. $R^4$ and/or $R^5$ can represent hydrogen or straight-chain or branched alkyl having up to 5 carbon atoms, cycloalkyl having 3 to 6 carbon atoms, for example cyclopropyl or cyclohexyl, or cycloalkylalkyl having 4 to 9, in particular 4 to 7, carbon atoms, for example cyclopropylmethyl or cyclohexylmethyl, or alternatively denote an optionally substituted phenyl-lower alkyl group whose alkyl chain can contain 1 to 4 carbon atoms and whose phenyl ring can be unsubstituted or mono- or disubstituted by lower alkoxy, in particular methoxy, or alternatively halogen, hydroxyl or lower alkyl. Substituents of the azepine ring prove to be advantageous in which D denotes a bond and one of the substituents $R^4$ and $R^5$ is hydrogen, for example $R^4$ denotes hydrogen or an alkyl, cycloalkyl or cycloalkylalkyl group having up to 5 carbon atoms and $R^5$ denotes hydrogen. If $R^4$ represents an optionally substituted phenyl-lower alkyl group, in particular optionally substituted benzyl, $R^5$ is preferably hydrogen. If $R^4$ and $R^5$, together with the nitrogen atom to which they are bonded, form a heterocycle, this can be a pyrrolidine, piperidine, morpholine or optionally substituted piperazine ring. Thus, for example, piperazine rings which are unsubstituted or substituted by optionally substituted phenyl are suitable.

According to the invention, the novel compounds of the formula I and their acid addition salts are obtained by a process in which, in a known manner a) to prepare compounds of the general formula Ia

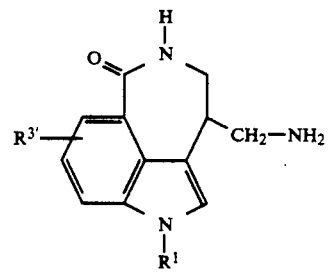

in which $R^1$ has the above meaning and $R^3$ has the meaning given for $R^3$ with the exception of hydroxyl, compounds of the general formula II

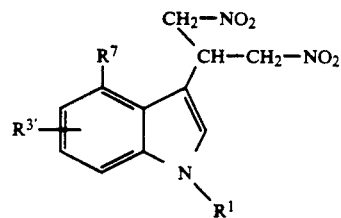

in which $R^1$ and $R^3$ have the above meaning and $R^7$ denotes a lower alkoxycarbonyl group or the CN group, are cyclized under reducing conditions, or b) to prepare compounds of the general formula Ib

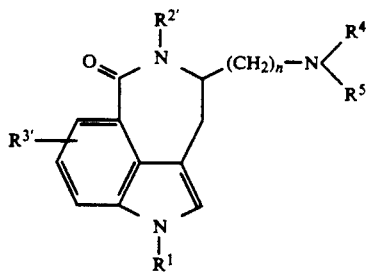

in which $R^1$, $R^{3'}$, $R^4$, $R^5$ and n have the above meanings, and represents hydrogen or lower alkyl, compounds of the general formula III

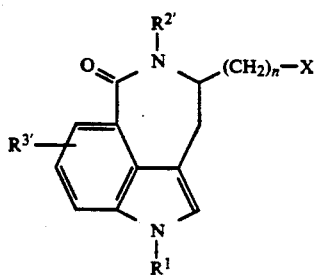

in which $R^1$, $R^{2'}$, $R^{3'}$ and n have the above meanings, and X represents a leaving group which can be removed nucleophilically, are reacted with compounds of the general formula IV

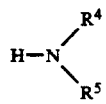

in which $R^4$ and $R^5$ have the above meaning, or c) to prepare compounds of the general formula Ic

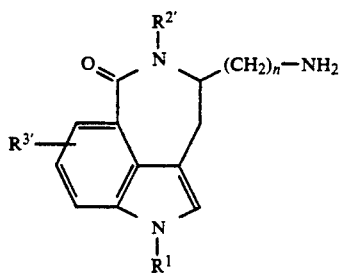

in which $R^1$, $R^2$, $R^3$ and n have the above meanings, the group Y in compounds of the general formula V

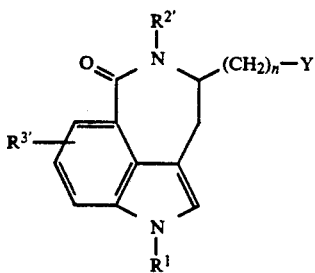

in which $R^1$, $R^{2'}$, $R^3$ and n have the above meanings, and Y represents an azide or phthalimide group or, if n is 1, Y may also represent the cyano group is converted into the amino group, or d) to prepare compounds of the general formula Id

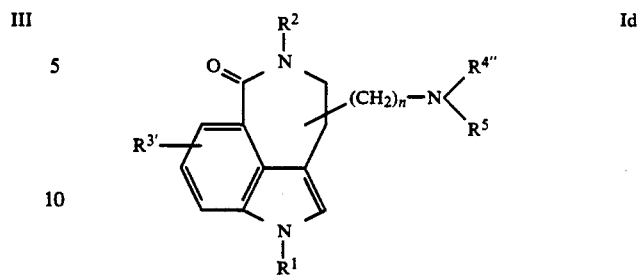

in which $R^1$, $R^2$, $R^{3'}$, $R^5$ and n have the above meanings, and $R^{5''}$ has the meaning given for $R^4$ with the exception of hydrogen, compounds of the general formula VI

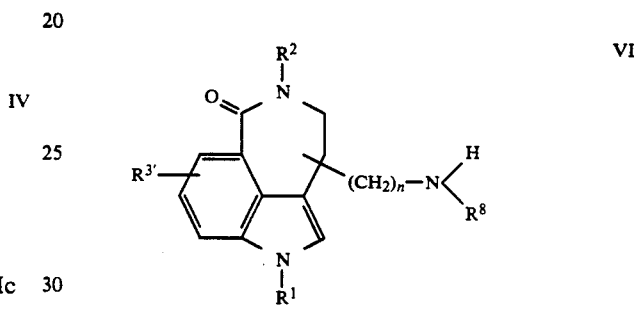

in which $R^1$, $R^2$, $R^{3'}$ and n have the above meanings, and $R^8$ denotes hydrogen, alkyl having 1 to 5 carbon atoms, cycloalkyl having 3 to 6 carbon atoms, cycloalkylalkyl having 4 to 9 carbon atoms, a phenyl-lower alkyl group optionally mono- or disubstituted in the phenyl ring by lower alkyl, lower alkoxy, hydroxyl or halogen, or an amino-protective group, are alkylated and a possible amino-protective group $R^8$ is removed again, or e) to prepare compounds of the general formula Ie

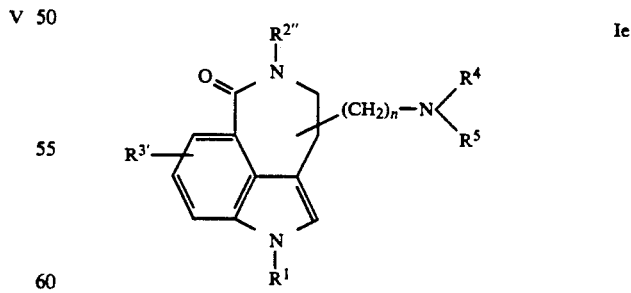

in which $R^1$, $R^{3'}$, $R^4$, $R^5$ and n have the above meanings, and $R^{2''}$ denotes a lower alkyl group optionally substituted in the α-position to the nitrogen atom by lower alkoxy, the 1-hydroxyalkyl group in compounds of the general formula VII

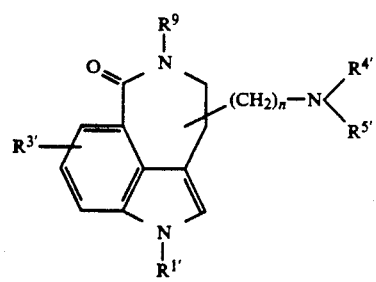

VII in which R³' and n have the above meanings, R¹' has the meaning given for R or represents an amino-protective group, R⁴' and R⁵' have the meanings given for R⁴ and R⁵, where, however, an NR⁴R⁵ group in which R⁴ and/or R⁵ denote hydrogen is protected by at least one easily removable amino-protective group in such a way that it does not react with acylating or alkylating agents, and R⁵ represents a lower 1-hydroxyalkyl group, is converted into the radical R⁴" and possible amino-protective groups are removed again, or f) to prepare compounds of the general formula If

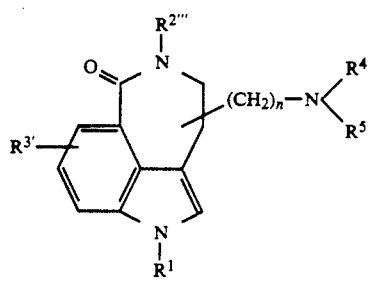

If in which R¹, R³', R⁴, R⁵ and n have the above meanings, and R²''' denotes lower alkyl, compounds of the general formula VIII

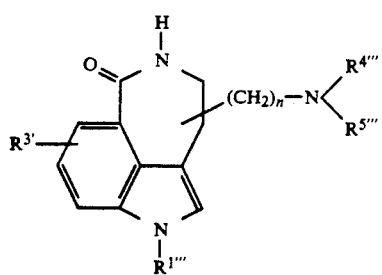

VIII in which R³' and n have the above meanings, and R¹''', R⁴''' and R⁵''' have the meanings given for R¹, R⁴ and R⁵ with the exception of hydrogen or represent an amino-protective group, are reacted with compounds of the general formula XII

R²'''—X   XII in which R²''' and X have the above meanings, and then possible amino-protective groups are removed again, or g) to prepare compounds of the general formula Ig

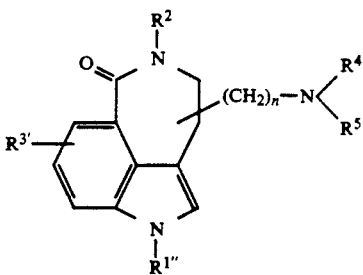

Ig in which R², R³, R⁴, R⁵ and n have the above meanings, and R¹'' has the meaning given for R¹ with the exception of hydrogen, compounds of the general formula IX

IX in which R², R³', R⁴', R⁵ and n have the above meanings, are reacted with compounds of the general formula X

R¹''—X   X in which R¹'' and X have the above meanings, and then possible amino-protective groups are removed again, or h) to prepare compounds of the general formula Ih

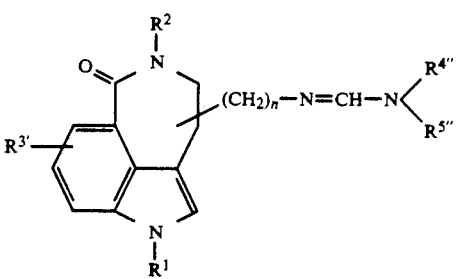

Ih in which R¹, R², R³', R⁴'' and n have the above meanings, and R⁵'' has the meaning given for R⁵ with the exception of hydrogen, there is introduced in compounds of the general formula Ii

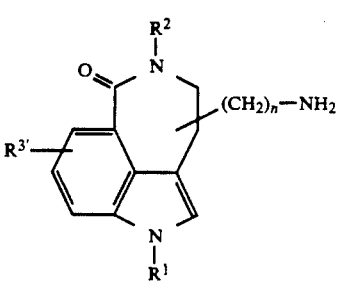

Ii in which $R^1$, $R^2$, $R^{3'}$ and n have the above meanings, the aminomethylene radical of the general formula b

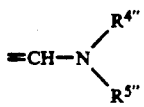

in which $R^{4''}$ and $R^{5''}$ have the above meanings, and, if desired, in resulting compounds of the formula I, in which $R^{3'}$ denotes methoxy and/or $R^1$, $R^4$ and/or $R^5$ contain a methoxyphenyl group, the methoxy group is cleaved to give the hydroxyl group and/or in resulting compounds of the formula I in which $R^1$, $R^4$, $R^5$ and/or $R^6$ represent an optionally substituted benzyl group, this benzyl group is removed by hydrogenolysis and, if desired, free compounds of the formula I are converted into their acid addition salts, or the acid addition salts are converted into the free compounds of formula I.

The reductive cyclization of compounds of the formula II to give compounds of the formula Ia according to process variant a) can be carried out in a known manner by treating compounds of the formula II with a reducing agent which is capable of selectively reducing aliphatic nitro groups to amino groups without subjecting the cyano or alkoxycarbonyl radical to reductive attack, in a solvent which is inert under the reaction conditions. Suitable reducing agents are, for example, hydrazine in the presence of Raney nickel or, if $R^7$ is not cyano, alternatively hydrogen in the presence of a hydrogenation catalyst, in particular palladium/carbon. Suitable solvents are, in particular, lower alcohols such as methanol or ethanol, which in the case of a hydrogenating treatment with hydrogen can also be employed in a mixture with water. The reduction with hydrazine in the presence of a Raney nickel catalyst can be carried out at temperatures between room temperature and about 80° C., preferably at the boiling temperature of the solvent. The reduction by catalytic hydrogenation can be carried out at a hydrogen pressure of 3 to 120 bar and temperatures between room temperature and about 120° C. Depending on the type of hydrogenation conditions, an optionally substituted benzyl radical $R^1$ may be removed as well during catalytic hydrogenation, so that in such a case reduction with hydrazine is preferably selected.

The reaction of compounds of the formula III with amino compounds of the formula IV according to process variant b) can be carried out by customary aminoalkylation methods. The reaction is advantageously carried out under basic conditions in an organic solvent which is inert under the reaction conditions.

Suitable nucleophilically removable radicals X in the compounds of the formula III are halogens such as chlorine, bromine or iodine or alternatively an acyloxy radical O-E in which E represents a lower alkanoyl radical or an organic sulfonic acid radical, for example the radical of a lower alkanesulfonic acid such as, for example, methanesulfonic acid or of aromatic sulfonic acids such as benzenesulfonic acid or benzenesulfonic acids substituted by lower alkyl or by halogen, for example toluenesulfonic acids or bromobenzenesulfonic acids. Suitable inert organic solvents are in particular dimethylformamide, lower alkanols such as ethanol, cyclic ethers such as dioxane or tetrahydrofuran, halogenated hydrocarbons, aromatic hydrocarbons or mixtures of the abovementioned solvents. To entrain the acid formed during the reaction, the reaction is advantageously carried out with addition of an organic or inorganic base. However, an excess of the amine of the formula IV can also be used and this can be utilized as an internal base. Examples of organic bases are tertiary organic amines, in particular tertiary lower alkylamines such as triethylamine, tripropylamines, N-lower alkylmorpholines or N-lower alkylpiperidines. Suitable inorganic bases are in particular alkali metal carbonates or bicarbonates. The reaction temperature can be between room temperature and 100° C. and the reaction is preferably carried out at elevated temperature, for example at temperatures between 50° and 80° C.

The preparation of amine compounds of the formula Ic according to process variant c) from corresponding azides, cyanides or phthalimides of the formula V can be carried out in a known manner according to methods customary for the conversion of azides, cyanides or phthalimides to the corresponding amines. Thus, for example, phthalimides of the formula V can be hydrolysed in a known manner and cleaved, for example by treating with hydrazine, to give the compounds of formula Ic. Azides and cyanides of the formula V can be reduced to the corresponding amine compounds in a known manner in a solvent which is inert under the reaction conditions. In this reaction, the reduction conditions must be selected such that the lactam function of the ring structure is not attacked. For the reduction of azides of the formula V, suitable methods are, for example, treatment with hydrazine in the presence of Raney nickel, treatment with zinc chloride in methanol, treatment with sodium borohydride in a two-phase system consisting of an aqueous phase and a water-immiscible organic solvent, for example a halogenated hydrocarbon such as dichloromethane or an aromatic hydrocarbon such as toluene, in the presence of a phase-transfer catalyst, for example a tetraalkylammonium salt such as tetraoctylammonium acetate, treatment with triphenylphosphine in aqueous medium or catalytic hydrogenation. Catalytic hydrogenation can be carried out in a known manner in a solvent which is inert under the reaction conditions, for example a lower alkanol, in the presence of a hydrogenation catalyst at a hydrogen pressure in the range from 1-50 bar. Suitable hydrogen catalysts are Raney nickel or, if $R^1$ does not represent an optionally substituted benzyl group, alternatively palladium on carbon. The reduction of a cyanide of the formula V is preferably carried out by catalytic hydrogenation in the presence of Raney nickel in a mixture of a lower alcohol and ammonia at a hydrogen pressure between 50 and 150 bar.

Compounds of the formula Id can be prepared by alkylation of compounds of the formula VI according to process variant d) by customary methods for alkylating amines. Thus, compounds of the formula Id are obtained by reaction of compounds of the formula VI with compounds of the general formula XIIIa

 XIIIa or, if $R^8$ in the compounds of the formula VI denotes hydrogen, alternatively with compounds of the general formula XIIIb

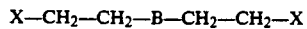 XIIIb in which B and X have the above meanings, and $R^{4IV}$ denotes alkyl having 1 to 5 carbon atoms, cycloalkyl having 3 to 6 carbon atoms, cycloalkylalkyl having 4 to 9 carbon atoms or a phenyl-lower alkyl group optionally mono- or disubstituted in the phenyl ring by lower alkyl, lower alkoxy, hydroxyl or halogen, under customary conditions for aminoalkylation or by reductive alkylation of the compounds of the formula VI with aldehydes or ketones of the formula XIIIc $$R^{4V}=O \qquad \text{XIIIc}$$

in which $R^{4V}$ represents a radical having at least 2 carbon atoms and corresponding to the radical $R^{4IV}$ but containing one fewer hydrogen atom.

The reaction of compounds of the formula VI with compounds of the formula XIIIa or XIIIb can be carried out under basic conditions by customary methods for alkylating amines in a solvent which is inert under the reaction conditions. It can be carried out, for example, in the manner described for the reaction of compounds of the formula III with compounds of the formula IV. If $R^8$ represents an amino-protective group, this can be a known protective group which is removable by hydrogenolysis or hydrolysis. Suitable protective groups removable by hydrogenolysis include, in particular, optionally substituted benzyl or benzhydryl groups which can subsequently be easily removed by hydrogenation, for example in the presence of a palladium/carbon catalyst. Suitable examples of amino-protective groups removable by hydrolysis include lower acyl groups such as formyl, acetyl or trifluoroacetyl. If $R^8$ in the compounds of the formula VI represents hydrogen, in the reaction with compounds of the formula XIIIa a mixture of mono- and disubstituted compounds is in general obtained in which the proportion of disubstituted compounds can vary depending on the amount of compound of the formula XIIIa employed and the reaction conditions. The monosubstituted and disubstituted compounds can be separated from one another in a known manner, for example by chromatography on silica gel.

Reductive alkylation of compounds of the formula VI can be carried out in a known manner by reaction of the compounds of the formula VI with an aldehyde or ketone of the formula XIIIc under reducing conditions. For example, the compounds of the formula VI can be reacted with compounds of the formula XIIIc in a solvent which is inert under the reaction conditions in the presence of a reducing agent, for example formic acid, a borane/di-lower alkylamine complex or sodium cyanoborohydride. The compounds of the formula VI, however, can also first be reacted with the compounds of the formula XIIIa in a solvent which is inert under the reaction conditions and the Schiff's bases formed as intermediates can then be reduced in situ or after isolation by treatment with a reducing agent which does not attack the lactam function of the ring structure. Reduction of the intermediate imine compounds can be carried out, for example, in a known manner by treatment with a borane/di-lower alkylamine complex, for example borane/dimethylamine, or a diborane/pyridine complex, using sodium borohydride in glacial acetic acid or using sodium cyanoborohydride in acidic or neutral medium, for example in acetic acid or a lower alcohol. If desired, the reduction of the Schiff's bases can also be carried out by catalytic hydrogenation. Catalytic hydrogenation can be carried out, for example, in the presence of Raney nickel or palladium/carbon in a lower alcohol under mild conditions, for example at a hydrogen pressure of 1–3 bar at room temperature.

Conversion of the 1-hydroxyalkyl radical $R^9$ of the compounds of the formula VII to a radical $R^{2''}$ according to process variant e) for the preparation of compounds of the formula Ie can be carried out by known methods. Thus, a hydroxyalkyl group $R^9$ can be reduced in a known manner to the corresponding alkyl group, or the hydroxyalkyl group $R^9$ can be etherified with a lower alcohol in a known manner under acidic conditions.

Reduction of the hydroxyalkyl group to the alkyl group can be carried out in an organic solvent which is inert under the reaction conditions with the aid of a hydride reducing agent which is capable of reducing the hydroxyalkyl group without attacking the lactam function. Suitable reducing agents are in particular sodium borohydride in the presence of strong organic acids, for example haloacetic acids such as trifluoroacetic acid, or alternatively triethylsilane. Suitable solvents are, for example, open-chain or cyclic ethers, in particular cyclic ethers such as tetrahydrofuran or dioxane, or halogenated hydrocarbons such as dichloromethane. The reaction can be carried out at slightly elevated temperature, for example at temperatures between about 30° and 100° C., preferably at the reflux temperature of the reaction mixture.

Etherification of the hydroxyalkyl group $R^9$ with a lower alcohol can be carried out under customary conditions for ether formation catalyzed by acids. Thus, a compound of formula VII, for example, can be reacted in a lower alcohol with the addition of catalytically active amounts of a strong acid. The reaction is advantageously carried out at elevated temperature, for example by heating the compound of formula VII in the lower alcohol at the reflux temperature of the reaction mixture. Suitable acids include inorganic acids such as sulfuric acid or strong organic acids, preferably organic sulfonic acids, for example lower alkanesulfonic acids such as, for example, methanesulfonic acid or aromatic sulfonic acids such as benzenesulfonic acid or benzenesulfonic acids substituted by lower alkyl or by halogen or alternatively haloacetic acids.

After conversion of the radical $R^9$ to a radical $R^{2''}$ has been carried out, possible amino-protective groups are removed in a known manner.

The reaction of compounds of the formula VIII. with compounds of the formula XII according to process variant f) can be carried out in a known manner under customary conditions for the alkylation of amides. Thus, the reaction can be carried out in a solvent which is inert under the reaction conditions in the presence of a strong base which is capable of deprotonating the nitrogen atom of the lactam group. Suitable bases are, for example, organolithium bases, for example a lower alkyllithium, in particular butyllithium, or lithium diisopropylamide, or potassium tert-butoxide. Suitable solvents are, for example, open-chain or cyclic ethers such as diethyl ether, tetrahydrofuran or dioxane. The reaction is advantageously carried out at temperatures in the range from −78° C. to room temperature. After reaction is complete, possible aminoprotective groups are removed again in a known manner.

The reaction of compounds of the formula IX with compounds of the formula X according to process variant g) can be carried out by customary methods for the alkylation of indoles. In the compounds of the formula X the nucleophilically removable radical X can have the meanings given above for the compounds of the formula III. Halogens, preferably iodine or bromine, are particularly suitable or alternatively organic sulfonic acid radicals. The reaction is advantageously carried out in an organic solvent which is inert under the reaction conditions in the presence of a strong base. Suitable strong bases are, for example, alkali metal hydrides such as sodium hydride or organolithium bases, for example a lower alkyllithium, in particular butyllithium, or lithium diisopropylamide, or potassium tert-butoxide. If $R^2$ denotes hydrogen, the more strongly nucleophilic indole nitrogen reacts first. In order to avoid an additional alkylation at the lactam nitrogen, the amount of base is preferably restricted such that it is insufficient for a second alkylation. If desired, a free amide group can also be protected in a known manner by introducing a formyl protective group which is removed again by hydrolysis during the subsequent working-up. Suitable solvents are dimethylformamide or open-chain or cyclic ethers such as diethyl ether, tetrahydrofuran or dioxane The reaction is advantageously carried out at elevated temperature, for example at temperatures between 30° and 100° C. Possible amino-protective groups can be removed after the reaction in a known manner.

The introduction of the aminomethylene radical of the formula b into the amino compounds of the formula Ii according to process variant h) can be carried out by customary methods for forming amidines. Thus, the compounds of the formula Ii can be reacted in a known manner with haloiminium salts of the general formula XIa

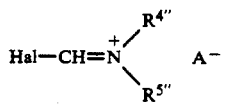

in which $R^{4''}$ and $R^{5''}$ have the above meanings, Hal denotes chlorine or bromine, and A represents an acid anion, or with acetals of the general formula XIb

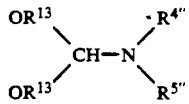

in which $R^{4''}$ and $R^{5''}$ have the above meanings, and $R^{13}$ denotes lower alkyl.

The reaction of compounds of the formula Ii with haloiminium salts of the formula XIa to give the compounds of the formula Ih can be carried out in a known manner under customary conditions for the formation of amidines. In the salts of the formula XIa A can represent the anion of a hydrolialic acid, in particular chloride. The reaction is advantageously carried out in an organic solvent which is inert under the reaction conditions, for example dimethylformamide, an open-chain or cyclic ether, a halogenated hydrocarbon or a mixture of these solvents, at temperatures from room temperature to 100° C.

The reaction of compounds of the formula Ii with acetals of the formula XIb can be carried out in a known manner under customary conditions for the formation of amidines, for example the conditions given above for reaction of the compounds of the formula Ii with the compounds of the formula XIa.

Amino-protective groups selected in the abovementioned compounds may be any known protective groups which can subsequently be removed again in a known manner by solvolysis or hydrogenolysis. Suitable amino-protective groups which can easily be removed again are known, for example, from E. Mc Omie "Protective Groups in Organic Chemistry" Plenum Press 1971. Suitable amino-protective groups include, for example, acyl groups which can be removed by hydrolysis, preferably the trifluoroacetyl group, or alternatively optionally substituted benzyl groups which can be removed again by hydrogenolysis in a known manner. The amino-protective groups must of course in each case be selected taking into account the other radicals contained in the compounds to be protected such that the amino group is adequately protected under the prevailing reaction conditions for the preparation and/or further processing of the compounds, and such that the protective groups are subsequently easily removable under conditions under which other radicals contained in the molecule are not attacked. The protective group which can be removed by hydrogenolysis used is preferably the benzyl group. The group which can be removed by hydrolysis employed is preferably the trifluoroacetyl group. If the $NR^4R^5$ group represents an $NH_2$ group, it is adequate when using the trifluoroacetyl protective group if one of the hydrogen atoms is replaced by this protective group. To introduce a trifluoroacetyl protective group, the compound to be protected can be reacted with trifluoroacetic anhydride in a known manner. If $R_2$ denotes hydrogen, an acylation on the amide nitrogen can in some cases also take place during this acylation, a lactam imide function being formed. A lactam imide function of this type, however, is cleaved again during a subsequent treatment of the acylation product with aqueous saturated sodium hydrogen carbonate solution for the neutralisation of acid formed and of excess acid anhydride. If the substituents $R^1$, $R^4$ and/or $R^5$ contain phenolic hydroxyl groups, these can be protected if desired during the above reactions by known ether protective groups, for example benzyl groups, which can subsequently be removed again.

In compounds of the formula I in which $R^3$ denotes methoxy and/or $R^1$ and/or $R^4$ and/or $R^5$ contain a methoxyphenyl group, the methoxy group can be cleaved to give the hydroxyl group using methods suitable for the cleavage of methoxyaryl ethers in a known manner. For example, the ether cleavage can be carried out by treatment with hydrogen iodide or hydrogen bromide in a solvent which is inert under the reaction conditions, for example acetic anhydride or acetic acid, or by treatment with iodotrimethylsilane in the presence of a base or with boron tribromide in a halogenated hydrocarbon such as dichloromethane.

In compounds of the formula I in which $R^1$ and/or $R^4$ and/or $R^5$ and/or $R^6$ represent a benzyl group which is optionally substituted in the phenyl ring, this group can be removed by hydrogenolysis if desired in a known manner. Hydrogenolysis can be carried out in a solvent which is inert under the reaction conditions, for example a lower alcohol, by catalytic hydrogenation at a hydrogen pressure of 3 to 50 bar and temperatures between room temperature and about 120° C. in the presence of a hydrogenation catalyst, for example palladium/carbon. The removal of benzyl can also be carried out by treatment with formic acid in the presence of palladium/carbon in a lower alcohol or by treatment with sodium in liquid ammonia.

The compounds of the formula I can be isolated from the reaction mixture and purified in a known manner. Acid addition salts can be converted into the free bases in a customary manner and these can be converted into pharmacologically acceptable acid addition salts if desired in a known manner.

Suitable pharmacologically acceptable acid addition salts of the compounds of the formula I include, for example, their salts with inorganic acids, for example hydrohalic acids, in particular hydrochloric acid, sulfuric acid or phosphoric acids, or with organic acids, for example lower aliphatic mono- or dicarboxylic acids such as maleic acid, fumaric acid, lactic acid, tartaric acid or acetic acid or sulfonic acids, for example lower alkanesulfonic acids such as methanesulfonic acid or benzenesulfonic acids optionally substituted in the benzene ring by halogen or lower alkyl, such as p-toluenesulfonic acid, or cyclohexylaminosulfonic acid.

The compounds of the formula I contain an asymmetric center in the position in which the side chain —$(CH_2)_n$—D—$NR^4R^5$ is bonded to the azepine ring, and can exist in several optically active enantiomeric forms or as a racemate. The present invention embraces both the racemic mixtures and the pure optical isomers of the compounds of the formula I.

If racemates of the starting compounds of the formulae III, V, VI, VII, VIII or IX are employed in the synthesis, the compounds of the formula I are obtained in the form of racemates. Starting from optically active forms of these starting compounds, optically active compounds of the formula I can be obtained. The optically active compounds of the formula I can be obtained from the racemic mixtures in a known manner, for example by chromatographic separation on chiral separating materials or by reaction with suitable optically active acids, for example tartaric acid or malic acid, and subsequently resolution into their optically active antipodes by fractional crystallisation of the salts obtained.

The starting compounds of the formula II are useful intermediates for the preparation of pharmacologically active compounds, for example the compounds of the formula I. The compounds of the formula II can be obtained in a known manner starting from indole compounds of the general formula XIV

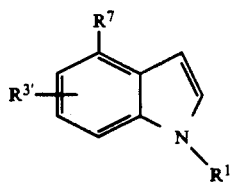

in which $R^1$, $R^{3'}$ and $R^7$ have the above meaning, by formylating the compounds of the formula XIV first to give aldehydes of the general formula XV

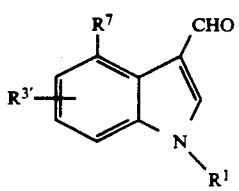

in which $R^1$, $R^{3'}$, and $R^7$ have the above meaning, and reacting the aldehyde compounds of the formula XV obtained with nitromethane.

The formylation of the indole compounds of the formula XIV can be carried out by reaction with known formylating agents by methods customary for the formylation of aromatics. For example, formylation may suitably be carried out with an N,N-disubstituted formamide such as dimethylformamide or N-methylformanilide in the presence of phosphorus oxychloride or phosgene according to the Vilsmeier method. The solvent used in this reaction can be an excess of dimethylformamide. Alternatively aromatic hydrocarbons such as benzene or chlorobenzene can be employed. The reaction can be carried out at temperatures between room temperature and about 80° C.

Aldehyde compounds obtained of the formula XV in which $R^1$ denotes hydrogen can be converted if desired by reaction with compounds of the formula X to those compounds of the formula XV in which $R^1$ represents a $R^1$ radical. The reaction can be carried out by customary methods for the alkylation of indoles and, for example, under the conditions given above for the reaction of compounds of formula IX with compounds of formula X.

The reaction of compounds of the formula XV with nitromethane can be carried out in the presence of a base under customary conditions for the reaction of aldehydes with C-H acidic compounds. The solvent used can be an excess of nitromethane. If desired, other organic solvents such as, for example, lower alcohols, halogenated hydrocarbons such as dichloromethane or cyclic ethers such as tetrahydrofuran can also be added. The reaction can be carried out at temperatures between room temperature and about 80° C. The bases employed can be inorganic or organic compounds which have a basic reaction. Thus, suitable compounds are, for example, alkali metal hydroxides, alkali metal carbonates or alkali metal acetates, ammonium acetate or ammonium carbonate, basic ion exchangers or tertiary organic bases such as, for example, tri-lower alkylamines or in particular 1,8-diazabicyclo[5.4.0]undec-7-ene(1.5-5)(=DBU) or 1,5-diazabicyclo[4.3.0]non-5-ene (=DBN). In the reaction, a mixture of the 3-(1,3-dinitropropan-2-yl)indole compounds of the formula II and the corresponding 3-(2-nitroethylene)indole compounds of the general formula XVI

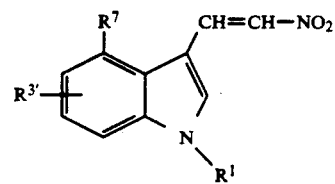

in which $R^1$, $R^{3'}$ and $R^7$ have the above meaning, can be formed. A mixture of compounds of the formula II and compounds of the formula XVI can be separated in a known manner, for example by distillation or by column chromatography. The ratio of compounds of the formula XVI to compounds of the formula II in the reaction mixture can be varied depending on the nature and strength of the base employed and the reaction conditions. In order directly to obtain compounds of the formula II or mixtures containing a very high proportion of compounds of the formula II, the bases employed are preferably 1,8-diazabicyclo[5.4.0]undec-7-ene (1.5-5) or 1,5-diazabicyclo[4.3.0]non-5-ene. In order to obtain compounds of the formula XVI or mixtures containing a very high proportion of compounds of the formula XVI, weak bases such as ammonium acetate are preferably employed.

Compounds of the formula XVI in which $R^1$ denotes hydrogen can be converted if desired into those compounds of the formula XVI in which $R^1$ denotes the radical $R^{1'}$ by reaction with compounds of the formula X. The reaction can be carried out by customary methods for the alkylation of indoles and, for example, under the conditions described above for the reaction of compounds of formula IX with compounds of formula X.

Compounds of the formula XVI can be converted to compounds of the formula II by reaction with further nitromethane in the presence of one of the bases given above as particularly suitable for the preparation of compounds of the formula II.

Compounds of the formula XVI can also be obtained by reacting compounds of the formula XIV with 1-nitro-2-dimethylaminoethylene.

The indole compounds of formula XIV are known or can be prepared by known methods or analogously to known methods. The preparation of compounds of formula XIV is described, for example, in U.S. Pat. No. 3,732,245.

The starting compounds of formula III are novel compounds which are useful intermediates for the preparation of pharmacologically active compounds, for example the compounds of the formula I. Compounds of the formula III can be obtained in a known manner from corresponding alcohols of the general formula XVII

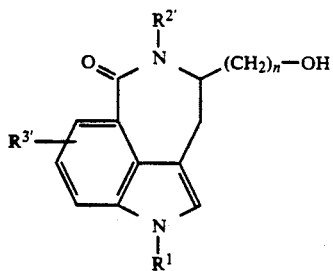
XVII in which $R^1$, $R^{3'}$, $R^{2'}$ and n have the above meanings, by converting the hydroxyl group to a leaving group X in a known manner. Thus, the compounds of the formula XVII can be reacted, for example to introduce a halogen radical X, with thionyl chloride or with phosphorus halides, for example phosphorus tribromide, in a known manner in a solvent which is inert under the reaction conditions, for example a halogenated hydrocarbon such as chloroform. Sulfonic acid radicals X can be introduced in a known manner by acylating compounds of the formula XVII with an appropriate sulfonyl halide. Thus, the alcohols of formula XVII can be reacted with a sulfonyl halide, preferably a sulfonyl chloride, under customary conditions for ester formation. For example, the reaction can be carried out in the presence of a base at temperatures between about room temperature and 100° C. in a solvent which is inert under the reaction conditions. Suitable bases include, for example, tertiary organic amines such as triethylamine or pyridine, which can be used at the same time as the solvents for the reaction.

Compounds of formula XVII are novel compounds which are useful intermediates for preparing pharmacologically active compounds, for example compounds of the formula I. The alcohols of the general formula XVIIa

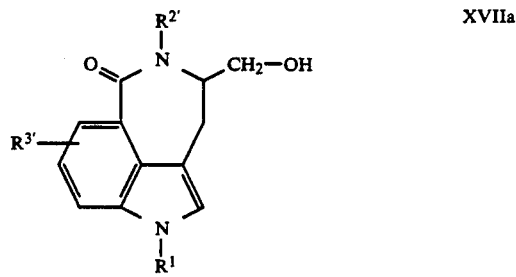
XVIIa in which $R^1$, $R^{2'}$ and $R^{3'}$ have the above meanings, can be obtained in a known manner by selectively reducing the ester group in corresponding esters of the general formula XVIII

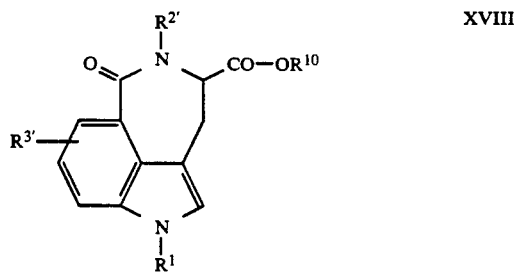
XVIII in which $R^1$, $R^{2'}$ and $R^{3'}$ have the above meanings, and $R^{10}$ denotes lower alkyl. Suitable reducing agents include, for example, hydride reducing agents capable of reducing esters, but which do not attack the lactam function of the ring structure. Thus, for example, it is possible to carry out the reduction with diisobutylaluminium borohydride or with alkali metal borohydrides such as sodium borohydride, lithium borohydride or lithium tri-lower alkyl borohydride or with sodium triethoxyaluminium hydride in a solvent mixture consisting of a cyclic ether such as tetrahydrofuran or dioxane and a lower alcohol at temperatures between room temperature and the reflux temperature of the reaction mixture. When using diisobutylaluminium hydride as the reducing agent, the reduction can be carried out in a cyclic ether such as tetrahydrofuran or aromatic hydrocarbons such as benzene or toluene at temperatures between −20° C. and room temperature.

Alcohols of the general formula XVIIb

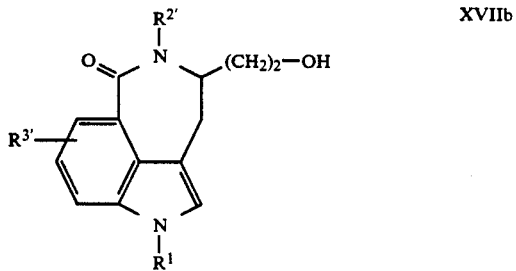
XVIIb in which $R^1$, $R^{2'}$ and $R^{3'}$ have the above meanings, can be obtained starting from those compounds of the formula V in which Y denotes the cyano group, by converting the cyano group in a known manner to an alkoxycarbonyl group and subsequently reducing this selectively to the hydroxy-methyl group. Suitable reducing agents include the hydride reducing agents listed above for the selective reduction of the ester group in the compounds of the formula XVIII.

Compounds of the general formula XVIIIa

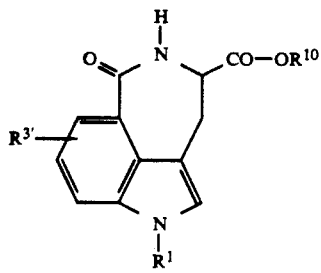

XVIIIa in which $R^1$, $R^{3'}$ and $R^{10}$ have the above meanings, can be prepared in a known manner starting from compounds of the general formula XIX

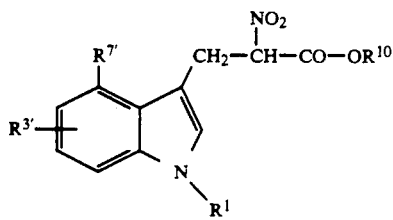

XIX in which $R^1$, $R^{4'}$ and $R^{10}$ have the above meanings, and $R^{7'}$ denotes a lower alkoxycarbonyl group, by reducing the compounds of the formula XIX under cyclizing conditions. For this purpose, the compounds of the formula XIX are treated in a solvent which is inert under the reaction conditions with a reducing agent which is capable of selectively reducing aliphatic nitro groups to amino groups without subjecting the alkoxycarbonyl radicals to reductive attack. Suitable reducing agents include, for example, hydrogen in the presence of a hydrogenation catalyst or hydrazine in the presence of Raney nickel. Reduction by catalytic hydrogenation can advantageously be carried out at a hydrogen pressure of 3 to 50 bar and temperatures between room temperature and about 120° C. A particularly suitable hydrogenation catalyst is palladium on carbon. Suitable solvents include, in particular, aromatic hydrocarbons such as toluene or xylene. Depending on the type of hydrogenation conditions, an optionally substituted benzyl ring $R^1$ can likewise additionally be removed in a catalytic hydrogenation by in this case preferably selecting the reduction using hydrazine. During the reduction of the compounds of the formula XIX under the aforementioned conditions, in general a mixture of compounds of the general formula XX

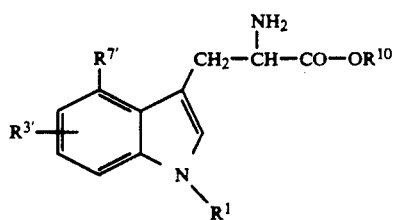

XX in which $R^1$, $R^{3'}$, $R^{7'}$ and $R^{10}$ have the above meanings, and the corresponding cyclized compounds of the formula XVIIIa is formed. To complete the cyclization, this mixture is preferably heated to temperatures between 100° and 150° C. for a period of 0.5 to 3 hours.

Compounds of the formula XVIIIa in which $R^1$ denotes hydrogen can, if desired, be converted by reaction with compounds of the formula X to compounds of formula XVIIIa in which $R^1$ denotes the radical $R^{1''}$. The reaction can be carried out by customary methods for alkylating indoles and, for example, under the conditions described above for the reaction of compounds of formula IX with compounds of formula X.

If desired, an alkyl group $R'''$ can be introduced into the compounds of the formula XVIIIa in a known manner. Thus, the compounds of the formula XVIIIa can be reacted with compounds of the formula XII under customary conditions for the alkylation of amides. The reaction can be carried out in a solvent which is inert under the reaction conditions in the presence of a strong base which is capable of deprotonating the nitrogen atom of the lactam group. Suitable bases include, for example, the bases mentioned above the alkylation of compounds of the formula VIII according to process f), in particular butyl-lithium. Suitable solvents include, for example, cyclic or open-chain ethers such as preferably tetrahydrofuran or dioxane or alternatively diethyl ether. The reaction is advantageously carried out at temperatures in the range from −80° C. to room temperature. If $R^1$ denotes hydrogen, the indole function must be protected in a known manner by a customary amino-protective group which is subsequently removed again.

Compounds of the formula XIX can be obtained in a known manner starting from compounds of the general formula XXI

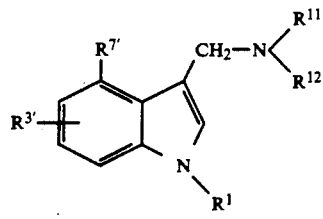

XXI in which $R^1$, $R^{3'}$ and $R^{7'}$ have the above meanings, and $R^{11}$ and $R^{12}$ each denote the lower alkyl or together represent an alkylene chain having up to 4 carbon atoms, by converting the $NR^{11}R^{12}$ group of the compounds of formula XXI to a leaving group which can be removed nucleophilically and reacting the reaction product in situ with a lower alkyl nitroacetate. Thus, for example, the compound of the formula XXI can be reacted with the alkyl nitroacetate in a solvent which is inert under the reaction conditions in the presence of a tri-lower alkylphosphine, in particular tributylphosphine, which reacts intermediately with the amino group f the compound of formula XXI to give a radical which can be removed nucleophilically. Suitable solvents include, for example, acetonitrile, dimethylformamide and cyclic ethers. The reaction is advantageously carried out at elevated temperature, for example at temperatures in the range from 50° to 80° C. If desired, the compound of the formula XXI can also first be converted to the corresponding quaternary ammonium salt by reaction with a lower alkyl iodide in a known manner, and the salt can subsequently be reacted with the lower alkyl nitroacetate.

Compounds of the formula XXI can be obtained from indole compounds of the general formula XIVa

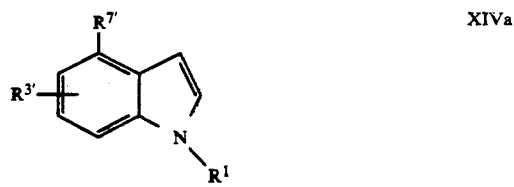

XIVa in which $R^1$, $R^{3'}$ and $R^{7'}$ have the above meanings, in a known manner by reacting the compounds of the formula XIVa with formaldehyde and an amine $HNR^{11}R^{12}$, in which $R^{11}$ and $R^{12}$ have the above meanings, by customary methods for amino methylation, for example, under the conditions of a Mannich reaction.

Compounds of the formula XIX can also be obtained from compounds of the general formula XXII

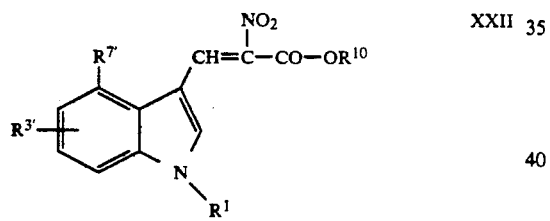

XXII in which $R^1$, $R^{3'}$, $R^{7'}$ and $R^{10}$ have the above meanings, by reducing the double bond in the compounds of formula XXII in a known manner, for example by treating a compound of formula XXII with sodium trimethoxyborohydride prepared in situ form sodium borohydride and methanol in tetrahydrofuran. Compounds of the formula XXII can be obtained in a known manner by reacting compounds of the general formula XVa

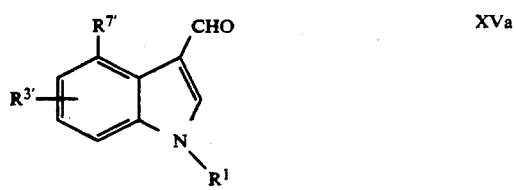

XVa in which $R^1$, $R^{3'}$ and $R^{7'}$ have the above meanings, with a lower alkyl nitroacetate. The reaction can be carried out by known methods in the presence of a base under customary conditions for the reaction of aldehydes with C-H acidic compounds, for example the conditions given above for the reaction of compounds of the formula XV with nitromethane.

Compounds of formula V are novel and are useful intermediate for preparing pharmacologically active compounds, for example the compounds of formula I.

Compounds of the formula V can be obtained by reacting corresponding compounds of formula III in a known manner with an alkalimetal azide, an alkali metal phthalimide or an alkali metal cyanide.

Compounds of the formula VI include those compounds of the formula I in which $R^4$ denotes hydrogen, D represents a bond, and $R^3$ does not represent hydroxyl or can be obtained by introducing an amino-protective group into corresponding compounds of the formula I in which $R^5$ denotes hydrogen.

Compounds of the formula VII are novel compounds which are useful intermediates for preparing pharmacologically active compounds, for example the compounds of the formula I. Compounds of formula VII can be obtained by acylating compounds of the general formula XXIII

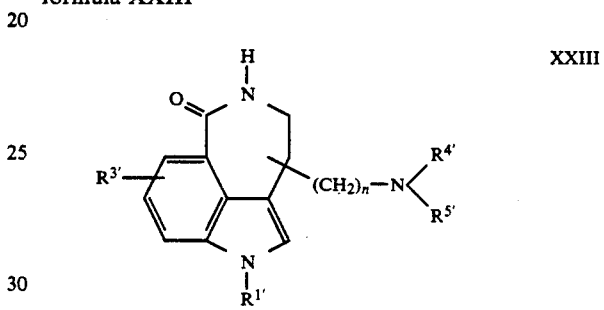

XXIII in which $R^{1'}$, $R^{3'}$, $R^{4'}$, $R^{5'}$ and n have the above meanings, in a known manner to give compounds of the general formula XXIV

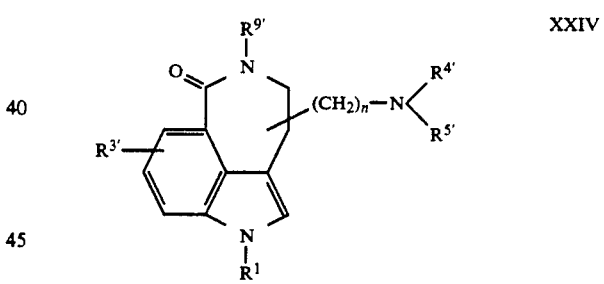

XXIV in which $R^1$, $R^{3'}$, $R^{4'}$, $R^{5'}$ and n have the above meanings, and $R^{9'}$ represents an acyl group corresponding to the radical $R^9$, and subsequently reducing the resulting compounds of formula XXIV to give the compounds of the formula VII.

For the acylation, the compounds of the formula XXIII can be reacted with an acylating agent of the general formula XXV

$R^{9'}-X'$   XXV in which $R^{9'}$ has the above meaning, and $X'$ denotes halogen or a lower alkoxycarbonyl group, at elevated temperatures, for example temperatures between 30° and 100° C. The solvent used can be an excess of the acylating agent, to which if desired further organic solvents such as open-chain or cyclic ethers, chlorinated hydrocarbons such as dichloromethane or aromatic hydrocarbons such as benzene can be added. Preferably, the acylating agent employed is the corresponding acid anhydride. A mixed anhydride formed in situ from formic acid and a lower carboxylic acid anhydride, preferably acetic anhydride, is preferably used for the formylation.

The reduction of compounds of the formula XXIV to compounds of the formula VII can be carried out in a known manner in an organic solvent which is inert under the reaction conditions with the aid of a hydride reducing agent which is capable of reducing the alkanoyl radical $R^{9'}$ of the mixed imide group of the compounds of the formula XXIV to the hydroxyalkyl group without attacking the lactam group of the oxoazepine ring structure or possible amide-protective groups. Reduction for example with di-lower alkylaluminium hydrides, in particular diisobutylaluminium hydride, diborane or di-lower alkyl borohydrides at low temperatures, for example temperatures between −80° C. and room temperature, proves suitable. Suitable solvents include, for example, open-chain or cyclic ethers such as diethyl ether or tetrahydrofuran, aromatic hydrocarbons such as benzene or toluene or halogenated hydrocarbons such as dichloromethane or mixtures of solvents of this type.

Compounds of the formula XXIII include compounds of the formula I in which $R^2$ denotes hydrogen, D represents a bond and $R^3$ does not represent hydroxyl and $R^4$ and/or $R^5$ do not denote hydrogen, or can be obtained from corresponding compounds of the formula I in which $R^4$, $R^5$ and/or $R^1$ denote hydrogen, by introduction of amino-protective groups in a known manner.

Compounds of the formula VIII include compounds of the formula I in which $R^2$ denotes hydrogen, D represents a bond and $R^3$ does not represent hydroxyl and the radicals $R^1$, $R^4$ and $R^5$ do not denote hydrogen, or can be obtained from corresponding compounds of the formula I in which $R^1$, $R^4$ and/or $R^5$ denote hydrogen, by introducing amino-protective groups in a known manner.

Compounds of the general formula IX include compounds of the formula I in which R denotes hydrogen, D represents a bond and $R^3$ does not represent hydroxyl and the radicals $R^4$ and $R^5$ do not denote hydrogen, or can be obtained from corresponding compounds of the formula I in which $R^4$ and/or $R^5$ denote hydrogen, by introducing an amino-protective group in a known manner.

Compounds of the general formula XXVI

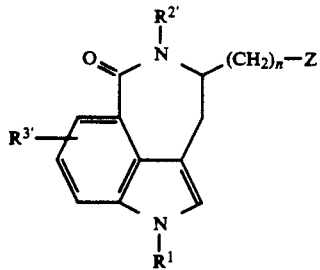

XXVI in which $R^1$, $R^{2'}$, $R^{3'}$ and n have the above meanings, and Z represents hydroxyl or one of the radicals X or Y defined above, include the compounds of the formulae III, V and XVII and are useful intermediates for preparing pharmacologically active compounds, for example the compounds of formula I.

The compounds of the formula I and their pharmacologically acceptable acid addition salts have interesting pharmacological properties and exhibit a selective affinity for 5-HT$_1$ receptors. They are distinguished in particular by an advantageous activity on the motility of the gastrointestinal tract, in particular of the stomach. Thus, in animal experiments the peristaltic waves of the stomach are amplified under the influence of compounds of the formula I, the frequency of the movements not being significantly changed. In addition, the compounds have a serotonin-agonistic stimulating action on 5-HT$_1$-like receptors in the basilar artery, which is a good index of an antimigraine activity of the compounds.

Description of Pharmacological Test Methods

1. Determination of the minimum toxic dose.

Male mice of 20-25 g weight are administered maximum doses of 300 mg/kg of the test substance p.o. The animals were carefully observed for 3 hours for symptoms of toxicity. Over a period of 72 hours after administration, all symptoms and cases of death are additionally recorded. Concomitant symptoms are likewise observed and recorded. If death or strong toxic symptoms are observed, further mice are administered increasingly lower doses until toxic symptoms no longer occur. The lowest dose which causes death or strong toxic symptoms is given in the following Table A as the minimum toxic dose. The example numbers given in Table A relate to the subsequent preparation examples.

2. Determination of effect on stomach motility in anaesthetised rats.

For the tests, groups of 5-6 fasting rats of the SIV 50 strain having a body weight of 220-290 g were used in each test which had been anaesthetised with a ketamine/xylazine mixture. The animals received an initial dose of 1 ml/kg of a solution of 50 mg/ml of ketamine and 10 mg/ml of xylazine administered i.p., and the anaesthetic level was maintained by a continuous intraperitoneal infusion of the same solution at an infusion rate of 1 ml/kg/h. The animals were tracheotomised and laparotomised. After applying a pylorus ligature, a stomach tube was inserted into the stomach and connected at the other end by means of a three-way tap to a calibrated pressure transducer (Statham Element P 23 ID). A corresponding tube was inserted rectally 8-9 cm into the colon and likewise connected in the same manner to a calibrated pressure transducer of the same type. The stomachs of the animals were then filled with 2 ml of water via the tube. After a stabilisation phase of 40 min, the pressure variations in the stomach and colon were measured over a test period of 2 hours and 20 minutes, and the amplitudes produced by the phasic gastric motility were recorded by means of a Watanabe multirecorder (MC 6621). The geometric mean values of the amplitudes during the first 20 min were determined for the individual animals and used as control amplitude values. After the first 20 min, the test substances were administered i.p. The maximum increase in amplitude (=mean value of the 20 minute period in which the highest increase in amplitude occurs) caused by the test substances was determined in % increase of the control amplitude values determined before administration of the test substances, and the mean value for the animal group is given in the following Table A. In addition, the maximum increase in the mean gastric tone caused by the test substances during the test period compared with the mean gastric tone existing before administration of the test substances was recorded. This increase in gastric tone is given in Table A in cm of H$_2$O (mean value of the animal group). In the colon, the test substances cause amplitude damping.

TABLE A

| | | Gastric Motility Promoting Effect in the Rat | | |
|---|---|---|---|---|
| Test Substance Example No. | Dose $\mu$mole/kg i.p. | Maximum Amplitude Increase (increase in % of control amplitude) | Gastric Tone Increase in cm $H_2O$ | Minimum Toxic Dose mg/kg Mouse p.o. |
| 1 | 10 | 449 | 7.4 | >300 |
| 2 | 100 | 239 | | >300 |
| 4 | 100 | 532 | 9.0 | >300 |
| 5a | 100 | 1129 | 9.5 | >300 |
| 5b | 100 | 449 | 3.8 | >300 |
| 6 | 100 | 609 | 15.4 | >300 |
| 8 | 100 | 569 | | >300 |
| 9 | 10 | 334 | 5.5 | >300 |
| 10 | 100 | 663 | 10.5 | >300 |
| 13 | 100 | 332 | 7.2 | >300 |
| 14 | 100 | 1115 | 3.0 | >300 |
| 15 | 100 | 308 | 3.1 | >300 |
| 17 | 100 | 293 | | >300 |
| 24 | 100 | 195 | | >300 |
| 25 | 100 | 206 | | 300 |
| 28 | 100 | 17 | 0.5 | >300 |
| 29 | 100 | 154 | | >300 |
| 31 | 100 | 928 | | >300 |
| 32 | 100 | 922 | | >300 |
| 34 | 100 | 467 | | |
| 36 | 100 | 351 | 11.5 | >300 |
| 37 | 100 | 950 | 4.0 | >300 |
| 38 | 100 | 559 | 12.4 | >300 |
| 39 | 100 | 569 | 1.8 | >300 |
| 40 | 100 | 997 | 6.5 | >300 |
| 41 | 100 | 234 | 2.7 | >300 |
| 45 | 100 | 580 | 3.5 | >300 |
| 47 | 100 | 1795 | 6.7 | |

3. Investigation of Properties Indicating Antimigraine Activity of Test Substance in vitro.

Migraine pains are associated with excessive dilation of the cranial vascular system. The test substances exhibit serotonin-agonistic effects and stimulate vascular contractions in 5-$HT_1$-like receptors in the basilar artery. This property of the test substances can be used as a basis for predicting anti-migraine activity. The serotoninagonistic activity of the substances on 5-$HT_1$-like receptors can be determined in vitro in isolated organ strips from the basilar artery of a pig. Serotonin produces a concentration -dependent contraction in isolated organ strips of porcine basilar artery due to stimulation of 5-$HT_1$-like receptors. Such a contraction is also produced by the test substances and is a good index of the antimigraine activity of the substances. The tests are carried out according to the method described by van Charldorp et al. (Naunyn-Schmiedeb. Arch. Pharmacol. supp. to volume 341, R89, 1990 and Eur. J. Pharmacol. 183, 1106–1107, 1990).

Experimental description of the in vitro determination of the effect inducing serotonin-agonistic contractions in segments of the isolated basilar artery of the pig.

For the experiment, helical segments of the basilar artery of pigs were used which were isolated from pig brains supplied by a slaughterhouse. Each strip was fixed in an organ bath consisting of 10 ml of a modified Tyrode solution such that the tissue was under a tension of 10 mN. Tyrode solution is an aqueous solution containing per liter 150.0 mmol of NaCl, 4.0 mmol of KCl, 1.8 mmol of $CaCl_2.2H_2O$, 1.1 mmol of $MgCl_2.6H_2O$, 25.0 mmol $NaHCO_3$, 0.3 mmol of $NaH_2PO_4.H_2O$ and 11.1 mmol of glucose. The solution was modified by adding $10^{-8}$ mol/l of indomethacin, $10^{-7}$ mol/l of atropine and $10^{-7}$ mol/l of propanolol and adjusted to pH=7.4. The bath was aerated with a mixture of 95% $O_2$ and 5% $CO_2$. After an equilibration phase of 1 hour a contraction of the tissue was produced twice, in each case by addition of serotonin at a concentration of $10^{-5}$ mol/l and the preparation was subsequently washed out. The contraction effect was then measured with increasing serotonin concentration and a cumulative concentration effect curve for serotonin was drawn up. A cumulative concentration effect curve was drawn up for the test substance on the same preparation (after washing out again).

In the following Table B, the maximum contraction caused by the test substances in relationship to the maximum contraction produced by serotonin, and the negative logarithm of that concentration of the test substance which produces 50% of the maximum contraction which can be produced by this test substance (=$pD_2$), and the relative potency calculated as $pD_2$ of the test substance relative to the $pD_2$ of serotonin determined on the same piece of artery are given.

TABLE B

| Example No. | Maximum Contraction Produced by Test Substance Relative to Maximum Contraction Produced by Serotonin = 1 | $pD_2$ = neg. log of Concentration Which Produces 50% of Maximum Contraction | Relative Potency $pD_2$ Test Substance / $pD_2$ Serotonin |
|---|---|---|---|
| 1 | 0.8 | 6.5 | 0.132 |
| 1a | 1.0 | 6.7 | 0.172 |
| 4 | 0.6 | 6.8 | 0.208 |
| 4a | 0.6 | 7.0 | 0.354 |
| 9 | 0.5 | 6.4 | 0.124 |
| 12 | 0.7 | 6.0 | 0.050 |

Due to their activity, the compounds of formula I and their physiologically acceptable acid addition salts are suitable in gastoenterology as medicaments for larger mammals, in particular humans, for the prophylaxis and treatment of motility disorders int he gastointestinal tract. Thus, the substances are useful, for example, for the treatment of various symptoms produced by motility disorders of the gastrointestinal tract such as nausea, sensation of fullness, stomach ache or irritable bowel syndrome. The compounds are also useful in the treatment and prophylaxis of migraine and related disorders and headaches caused by dilation of the cranial vascular system and in this case also have analgesic effects.

The doses to be used may be different from person to person and vary naturally depending on the type of the condition to be treated, the substance used and the form of administration. For example, parenteral formulations will in general contain less active substance than oral preparations. In general, however, pharmaceutical forms having an active substance content of 25 to 300 mg per individual oral dose are suitable for administration to larger mammals, in particular humans.

As medicines, the compounds of the formula I can be present with customary pharmaceutical auxiliaries in pharmaceutical preparations, such as, for example, tablets, capsules, suppositories or solutions, for example injection solutions or solutions for oral administration or sublingual administration, for example in spray form. These pharmaceutical preparations can be prepared by known methods using customary solid excipients such as, for example, lactose, starch or talc or liquid paraffins and using customary pharmaceutical adjuvants, for example tablet disintegrating agents, solubilizers or preservatives.

The following examples are intended to illustrate the invention in greater detail, without limiting its scope.

EXAMPLE 1

3-Aminomethyl-3,4,5,6-tetrahydro-6-oxo-1H-azepino[5,4,3-cd]indole

A) 90 ml of phosphorous oxychloride were added dropwise over the course of 30 minutes, while cooling in ice, to a solution of 100 g of methyl indole-4-carboxylate in 1000 ml of dimethylformamide. The ice bath was then removed and the reaction mixture was stirred at room temperature for a further 3 hours. To work up the reaction mixture it was then diluted with 1000 ml of dichloromethane while cooling in ice and stirring vigorously. Then 200 ml of water and 100 ml of 40% strength sodium hydroxide solution were added sufficiently slowly for the temperature not to rise above 40° C. The organic phase was separated, washed twice with 50 ml portions of 10% strength sodium hydroxide solution, dried over sodium sulfate and concentrated. The crude methyl 3-formylindole-4-carboxylate which remained as an oily residue was taken up in diethyl ether. The product crystallized out of the ethereal solution and was filtered out. Drying resulted in 83.4 g of methyl 3-formylindole-4-carboxylate with a melting point of 134°-135° C.

B) 60 g of the product obtained above were mixed at room temperature while stirring with 350 ml of nitromethane and 5 ml of 1,8-diazabicyclo[5.4.0]undec-7-ene (1.5-5) (=DBU), and the reaction mixture was left to react at a temperature of 65° C. for 6 hours. To work up the reaction mixture it was subsequently evaporated to dryness and the residue was dissolved in ethyl acetate. The solution was washed twice with water, dried over sodium sulfate, filtered and concentrated. The crude methyl 3-(1,3-dinitro-2-propyl)indole-4-carboxylate which remained as an oily residue was dissolved in diethyl ether. The product crystallized out of the ethereal solution. The crystals were filtered out, washed with diethyl ether and dried 67 g of methyl 3-(1,3-dinitro-2-propyl)indole-4-carboxylate were obtained with a melting point of 110° to 112° C.

C) 67 g of the product obtained above were dissolved in one liter of methanol 5 g of Raney nickel were added to the solution. 150 ml of hydrazine hydrate were then added dropwise to the reaction mixture. During this the temperature rose to 40° C. with vigorous evolution of gas. The reaction mixture was subsequently heated at a temperature of 55° C. for 1½ hours. To work up the reaction mixture it was cooled, filtered to remove the catalyst and evaporated to dryness. The crude title compound which remained as residue was purified by column chromatography on silica gel under slightly elevated pressure (flash chromatography) using methanol/25% strength aqueous ammonia solution 96:4 as the eluent. The foamy residue remaining after removal of the solvent mixture by evaporation was taken up in methanol and crystallized. The crystals were filtered out with suction and washed with a 9:1 methanol/diethyl ether mixture and dried 36.4 g of 3-aminomethyl-3,4,5,6-tetrahydro-6-oxo-1H-azepino[5,4,3-cd]indole hydrate were obtained with a melting point of 119° to 120° C.

For conversion into the hydrochloride, 13 g of the hydrate of the title compound obtained above were dissolved in 200 ml of methanol. An excess of ethereal hydrochloric acid solution was added to the solution dropwise while stirring. The crystals which formed at room temperature were filtered out and washed with a 9:1 methanol/diethyl ether mixture and dried. 12 q of 3-aminomethyl-3,4,5,6-tetrahydro-6-oxo-1H-azepino[5,4,3-cd]indole hydrochloride hydrate were obtained with a melting point of 193° to 204° C.

D) Separation of enantiomers:
The racemic title compound was fractionated as follows into its optical antipodes.

1a) 3R(+)-3-Aminomethyl-3,4,5,6-tetrahydro-6-oxo-1H-azepino[5,4,3-cd]indole and 1b) 3S(−)-3-Aminomethyl-3,4,5,6-tetrahydro-6-oxo-1H-azepino[5,4,3-cd]indole Da1) 8.2 g of racemic 3-aminomethyl-3,4,5,6-tetrahydro-6-oxo-1H-azepino[5,4,3-cd]indole hydrate were dissolved in 50 ml of methanol at the reflux temperature of the methanol, and 5.12 g of D(−)-tartaric acid were added to the stirred solution. Then 5 ml of water were added and the reaction mixture was stirred in a water bath at a temperature of 70° C. until a clear solution was obtained. This solution was stirred in an open vessel at room temperature for 24 hours. The crystals which formed were separated from the mother liquor and washed with a little methanol. Drying resulted in 5.9 g of crystals which were recrystallized from methanol/water 9:1 and dried 3 5 g 3R(+)-3-aminomethyl-3,4,5,6-tetrahydro-6-oxo-1H-azepino[5,4,3-cd]indole D-tartrate were obtained with a specific optical rotation $[\alpha]_D^{25} = +92.8°$ (c=0.25 in water).

Da2) 2.12 g of the tartrate obtained above were dissolved in 6.3 ml of water at a temperature of 95° C. The solution had a pH of 3.5. The pH of the solution was reduced to 0.5 by adding 25% strength isopropanolic hydrochloric acid solution, and the solution was subsequently concentrated to 4 ml under reduced pressure (water pump vacuum). The crystals which formed were filtered out after 24 hours from the aqueous reaction mixture, washed with a little ethanol and dried. 0.94 g of 3R(+)-3-aminomethyl-3,4,5,6-tetrahydro-6-oxo-1H-azepino[5,4,3-cd]indole hydrochloride was obtained with a melting point of 295° C. (decomposition) and a specific optical rotation of $[\alpha]_D^{25} = +232.4°$ (c=0.25 in water).

Da3) The aqueous filtrate remaining in Da2) was adjusted to a pH of 11 by adding saturated aqueous sodium carbonate solution and subsequently evaporated under reduced pressure (water pump vacuum). The remaining residue was purified by chromatography under slightly increased pressure (flash chromatography) on silica gel using methanol/25% strength aqueous ammonia solution 96:4 as eluent. 0.32 g of amorphous 3R(+)-3-aminomethyl-3,4,5,6-tetrahydro-6-oxo-1H-azepino[5,4,3-cd]indole was obtained with a specific optical rotation of $[\alpha]_D^{22} = +104°$ (c=1 in methanol).

Db1) The mother liquor obtained in step Da1) was evaporated and the residue was dissolved in 20 ml of water at a temperature of 80° C. The solution was cooled to room temperature, and then 4 ml of isopropanol were added. The solution was stirred in an open vessel at room temperature for 48 hours. The resulting crystals were filtered out, dried and recrystallized twice from water/isopropanol 20:4. 1.05 g of 3S(−)-3-aminomethyl-3,4,5,6-tetrahydro-6-oxo-1H-azepino[5,4,3-cd]indole D-tartrate were obtained with a specific optical rotation of $[\alpha]_D^{25} = -143°$ (c=1 in methanol).

Db2) 0.95 g of the tartrate obtained above was converted directly into the corresponding hydrochloride analogously to the method described in step Da2) 0.3 g of 3S(−)-3-aminomethyl-3,4,5,6-tetrahydro-6-oxo-1H-azepino[5,4,3-cd]indole hydrochloride was obtained with a specific optical rotation of $[\alpha]_D^{25} = -222°$ (c=0.25 in water).

Db3) Analogously to the method described in step Da3), the base was liberated from the aqueous filtrate remaining in process stage Db2) and was purified. 0.15 g of amorphous 3S(−) -3-aminomethyl-3,4,5,6-tetrahydro-6-oxo-1H-azepino[5,4,3-cd]indole was obtained with a specific optical rotation of $[\alpha]_D^{25} = -103°$ (c=1 in methanol).

EXAMPLE 2

3-Benzylaminomethyl-3,4,5,6-tetrahydro-6-oxo-1H-azepino[5,4,3-cd]indole 6.2 g of 3-aminomethyl-3,4,5,6-tetrahydro-6-oxo-1H-azepino[5,4,3-cd]indole hydrate (see Example 1C for preparation) were added to 120 ml of benzene, and 3.3 ml of benzaldehyde were added to the mixture. This reaction mixture was heated to boiling with a water trap for 3 hours. The reaction mixture was subsequently evaporated to dryness. The crude 3-benzylideneaminomethyl-3,4,5,6-tetrahydro-6-oxo-1H-azepino[5,4,3-cd]indole which remained as an oily residue was immediately processed further. To do this it was dissolved in 40 ml of glacial acetic acid, and 1.2 g of sodium borohydride were added in portions to the stirred solution while cooling in ice. The reaction mixture was then stirred at room temperature for 30 minutes. To work up, the glacial acetic acid was distilled off under reduced pressure (water pump vacuum). The remaining oily residue was taken up in 100 ml of water, and the mixture was basified to pH 9 by adding saturated aqueous sodium carbonate solution. The crude title compound which separated out as an oil was separated, and the aqueous phase was extracted three more times with 100 ml portions of methylene chloride. The organic phases were combined, dried over sodium sulfate, filtered and evaporated to dryness. The remaining crude product was purified by column chromatography on silica gel under slightly elevated pressure (flash chromatography) using ethyl acetate/methanol 4:1 as eluent. Evaporation of the eluent resulted in 7 g of 3-benzylaminomethyl-3,4,5,6-tetrahydro-6-oxo-1H-azepino[5,4,3-cd]indole as foam-like product.

3 g of the title compound obtained above were dissolved in methanol and converted into its hydrochloride as described in Example 1C). 2.9 g of 3-benzylaminomethyl-3,4,5,6-tetrahydro-6-oxo-1H-azepino[5,4,3-cd]indole hydrochloride were obtained with a melting point of 179° to 181° C.

EXAMPLE 3

3-(N-Benzyl-N-methylaminomethyl)-3,4,5,6-tetrahydro-6-oxo-1H-azepino[5,4,3-cd]indole 6.2 g of 3-benzylaminomethyl-3,4,5,6-tetrahydro-6-oxo-1H-azepino[5,4,3-cd]indole (see Example 2 for preparation) were dissolved in 250 ml of dimethylformamide. 0.81 ml of methyl iodide and 1.81 g of potassium carbonate were added to the stirred solution at room temperature. The reaction mixture was stirred at room temperature for 3 hours. Subsequently, to work up, the dimethylformamide was stripped off under reduced pressure (oil pump vacuum) at 50° C. The remaining oily residue was taken up in a mixture of equal parts of water and dichloromethane, the dichloromethane phase was separated, and the aqueous phase was extracted twice more with dichloromethane. The organic phases were combined, dried over sodium sulfate, filtered and evaporated. 3.84 g of oily crude product remained as residue. This was purified by chromatography under moderately elevated pressure (=low pressure chromatography =LPLC under 3 to 6 bar) on silica gel (proprietary product LiChroprep® Si 60) using dichloromethane/methanol 9:1 as eluent. 3.26 g of oily 3-(N-benzyl-N-methylaminomethyl)-3,4,5,6-tetrahydro-6-oxo-1H-azepino[5,4,3-cd]indole were obtained.

0.88 g of the title compound obtained above was dissolved in 5 ml of isopropanol, heating gently. A solution of 0.44 g of fumaric acid in a mixture of 9 ml of isopropanol and 1 ml of methanol was added to this solution 1 ml of methyl tert.-butyl ether was then added to this mixture until slightly turbid. The fumarate crystallized out of this reaction mixture. Removal of the crystals by filtration, washing with methyl tert.-butyl ether and drying resulted in 1.07 g of 3-(N-benzyl-N-methylaminomethyl)-3,4,5,6-tetrahydro-6-oxo-1H-azepino[5,4,3-cd]indolehydrogen fumarate semihydrate with a melting point of 191° to 193° C.

EXAMPLE 4

3-Methylaminomethyl-3,4,5,6-tetrahydro-6-oxo-1H-azepino[5,4,3-cd]indole

A1) 2.38 g of 3-(N-benzyl-N-methylaminomethyl)-3,4,5,6-tetrahydro-6-oxo-1H-azepino[5,4,3-cd]indole (see Example 3 for preparation) were dissolved in 150 ml of methanol. A spatula tip of a palladium/carbon catalyst (10%) was added to the solution under a stream of nitrogen. The mixture was subsequently hydrogenated in an autoclave under a hydrogen pressure of 3.5 bar at a temperature of 50° C. while stirring. After 3 hours the hydrogen was discharged, the reaction mixture was flushed with nitrogen and the catalyst was filtered out. The remaining solution was evaporated and the oily crude product remaining as residue was purified by low pressure chromatography on silica gel using methanol/25% strength aqueous ammonia solution 96:4 as eluent. 0.9 g of 3-methylaminomethyl-3,4,5,6-tetrahydro-6-oxo-1H-azepino[5,4,3-cd]indole was obtained as a foam-like product.

0.62 g of the title base obtained above was converted into the hydrochloride as described in Example 1C). 0.56 g of 3-methylaminomethyl-3,4,5,6-tetrahydro-6-oxo-1H-azepino[ 5,4,3-cd]indole hydrochloride was obtained with a melting point of 274° to 277° C.

A2) It is also possible in place of 3-(N-benzyl-N-methylaminomethyl)-3,4,5,6-tetrahydro-6-oxo-1H-azepino[5,4,3-cd]indole to employ as starting compound 3-(N-diphenylmethyl-N-methylamino)-3,4,5,6-tetrahydro-6-oxo-1H-azepino[5,4,3-cd]indole (melting point 192° C. with decomposition) which can be obtained analogously to Example 3 starting from 3-[N-(diphenylmethyl)aminomethyl]-3,4,5,6-tetrahydro-6-oxo-1H-azepino[5,4,3-cd]indole (melting point of the hydrochloride 291° C. with decomposition, preparation analogously to Example 2 starting from 3-aminomethyl-3,4,5,6-tetrahydro-6-oxo-1H-azepino[5,4,3-cd]indole hydrate and benzophenone).

B) Separation of enantiomers

The racemic title compound can be fractionated into its optical antipodes analogously to the method described in Example 1D. The following were obtained:

4a) 3R(+)-3-methylaminomethyl-3,4,5,6-tetrahydro-6-oxo-1H-azepino[5,4,3-cd]indole hydrochloride, melting point 310° C. (decomposition), $[\alpha]_D^{25} = 218.6°$ (c=1 in methanol) and 4b) 3S(−)-3-methylaminomethyl-3,4,5,6-tetrahydro-6-oxo-1H-azepino[5,4,3-cd]indole hydrochloride, melting point >280° C. (decomposition) $[\alpha]_D^{25} = -224.9°$ (c=1 in methanol).

C) Separation of enantiomers, 2nd method:

Ca1) 2.14 g of N-ethoxycarbonyl-L-leucine and 2.94 ml of triethylamine were dissolved in 75 ml of dry tetrahydrofuran. The solution was cooled to about −15° C. A solution of 1.37 ml of isobutyl chloroformate in 10 ml of dry tetrahydrofuran was then added, distributed over a period of 10 minutes, under a nitrogen atmosphere. The reaction mixture was stirred for a further 10 minutes. Then 2.8 g of racemic 3-methylaminomethyl-3,4,5,6-tetrahydro-6-oxo-1H-azepino[5,4,3-cd]indole were added in portions distributed over a period of 15 minutes at a temperature of about −15° C. The reaction mixture was then slowly warmed to room temperature and stirred for a further 3 hours. It was subsequently evaporated under reduced pressure, and the residue was purified by chromatography under slightly elevated pressure (flash chromatography) using ethyl acetate/methanol 99:1 as eluent. 3 g of the purified product were separated into the (+) and (−) enantiomers by preparative high-pressure liquid chromatography (HPLC).

Ca2) 1.8 g of the (+)-enantiomer were dissolved in 25 ml of concentrated hydrochloric acid and the solution was heated in an oil bath at 100° C. After 24 hours, the solution was evaporated under reduced pressure, and the residue was taken up in ethanol and again evaporated. The remaining residue was taken up in aqueous ethanol, and 1.18 g of potassium carbonate were added. The mixture was concentrated under reduced pressure, and the remaining residue was purified by chromatography under slightly elevated pressure (flash chromatography) using methanol/aqueous ammonia solution 99.5:0.5 as eluent. The resulting syrup-like product was dissolved in a little absolute ethanol, and an excess of ethanolic hydrochloric acid solution was added to the solution. The precipitate which formed was filtered out with suction and washed with absolute ethanol and diethyl ether. The resulting 3R(+)-3-methylaminomethyl-3,4,5,6-tetrahydro-6-oxo-1H-azepino[5,4,3-cd]indole hydrochloride had a melting point of 310° C. (decomposition) and a specific optical rotation $[\alpha]_D^{25} = +218.6°$ (methanol).

Cb) The (−) enantiomer obtained in process stage Ca1) was converted analogously to the method described in process stage Ca2) into the 3S(−)-3-methylaminomethyl-3,4,5,6-tetrahydro-6-oxo-1H-azepino[5,4,3-cd]indole hydrochloride with a melting point of >280° C. (decomposition) and a specific optical rotation $[\alpha]_D^{25} = -224.9°$ (methanol).

EXAMPLE 5 a) 3-Ethylaminomethyl-3,4,5,6-tetrahydro-6-oxo-1H-azepino[5,4,3-cd]indole, and b) 3-Diethylaminomethyl-3,4,5,6-tetrahydro-6-oxo-1H-azepino[5,4,3-cd]indole A) 6 g of 3-aminomethyl-3,4,5,6-tetrahydro-6-oxo-1H-azepino[5,4,3-cd]indole hydrate (see Example 1C for preparation) were dissolved in 60 ml of dimethylformamide. A total of 2.5 ml of ethyl bromide and 5.1 ml of triethylamine was added in four equal portions distributed over a period of 6.5 hours to the solution. During this time, the temperature of the reaction mixture was maintained at 60° C. To work up the reaction mixture it was evaporated to dryness, and the remaining crude mixture of the two title compounds was fractionated by chromatography under slightly elevated pressure (flash chromatography) on silica gel using dichloromethane/methanol/diethylamine 80:17:3. 3.4 g of oily monoethylaminomethyl crude product (=compound 5a) and 4.1 g of oily diethylaminomethyl crude product (=compound 5b) were obtained.

The oily crude product 5a) was dissolved in methanol. 2.3 g of 3-ethylaminomethyl-3,4,5,6-tetrahydro-6-oxo-1H-azepino[5,4,3-cd]indole with a melting point of 90° to 92° C. were crystallized out of the solution with the addition of a little diethyl ether.

The oily crude product 5b) was dissolved in ethanol, and the hydrochloride was prepared as described in Example 1C) by adding ethereal hydrochloric acid solution. 2.5 g of 3-diethylaminomethyl-3,4,5,6-tetrahydro-6-oxo-1H-azepino[5,4,3-cd]indole hydrochloride were obtained with a melting point of 150° to 153° C.

EXAMPLE 6

3-Isopropylaminomethyl-3,4,5,6-tetrahydro-6-oxo-1H-azepino[5,4,3-cd]indole 0.82 g of borane-dimethylamine complex was added to a stirred solution of 3-aminomethyl-3,4,5,6-tetrahydro-6-oxo-1H-azepino[5,4,3-cd]indole hydrate (see Example 1C for preparation) in 80 ml of tetrahydrofuran. The solution was heated under reflux for 1 hour and subsequently, at a temperature of 45° C., 10 ml of acetone were added dropwise. The reaction mixture was stirred at a temperature of 60° C. for 2.5 hours. To work up the reaction mixture it was subsequently evaporated to dryness, and the residue was dissolved in a mixture of water and dichloromethane. The dichloromethane phase was separated, and the aqueous phase was extracted three more times with 50 ml portions of a 9:1 dichloromethane/methanol mixture. The organic phases were combined and evaporated to dryness. The crude product which remained as residue was purified by chromatography under slightly elevated pressure (=flash chromatography) on silica gel using methanol/ethyl acetate 4:1 as eluent. The title compound was obtained as an oil.

The oily title compound was converted into its hydrochloride by the method described in Example 1C). 1.6 g of 3-isopropylaminomethyl-3,4,5,6-tetrahydro-6-oxo-1H-azepino[5,4,3-cd]indole hydrochloride were obtained with a melting point of 180° to 183° C.

EXAMPLE 7

4-Aminomethyl-3,4,5,6-tetrahydro-6-oxo-1H-azepino[5,4,3-cd]indole

A) 100 g of methyl indole-4-carboxylate were dissolved in 500 ml of glacial acetic acid. To the solution were added dropwise at room temperature a mixture of 86 ml of a 40% strength aqueous dimethylamine solution, 55 ml of a 37% strength aqueous formaldehyde solution and 250 ml of glacial acetic acid. The reaction mixture was subsequently stirred at room temperature for 20 hours. To work up the reaction mixture it was cooled in ice and 20% strength aqueous sodium hydroxide solution was added until pH 9 was reached. This was followed by extraction three times with dichloromethane, and the combined organic extracts were dried with sodium sulfate, filtered and concentrated. 127 g of crude methyl 3-dimethylaminomethylindole-4-carboxylate were obtained as a pale yellow oil.

B) 127 g of the product obtained above were dissolved in 600 ml of acetonitrile 68 ml of ethyl nitroacetate were added to the solution. Then, at room temperature, a solution of 40 ml of tributylphosphine in 350 ml of acetonitrile was added dropwise. The reaction mixture was heated at the reflux temperature for 2.5 hours. The reaction mixture was subsequently worked up by evaporating to dryness and dissolving the residue in 10% strength aqueous hydrochloric acid. The solution was extracted three times with ethyl acetate, and the combined organic extracts were dried over sodium sulfate, filtered and concentrated. The remaining crude product was purified by column chromatography on silica gel under slightly elevated pressure (flash chromatography) using cyclohexane/ethyl acetate 2:1 as eluent. The residue remaining after evaporation of the eluent was crystallized from diethyl ether. 66 g of methyl 3-(1-ethoxycarbonyl-2-nitropropyl)-indole-4-carboxylate were obtained with a melting point of 106°-110° C.

C) 66 g of the product obtained above were dissolved in 2 l of toluene. 5 g of palladium/carbon catalyst (10%) were added to the solution. The reaction mixture was subsequently hydrogenated under a hydrogen pressure of 50 bar at a temperature of 70° C. for 6 hours. The mixture was subsequently cooled, the catalyst was removed by filtration and the filtrate was evaporated. The remaining oily residue was heated at 130° C. for 1 hour to complete the cyclization. The crystals which formed on subsequent cooling were triturated with ethanol, filtered out and washed with a 1:1 diethyl ether/ethanol mixture. Drying resulted in 41.5 g of ethyyl 3,4,5,6-tetrahydro-6-oxo-1H-azepino[5,4,3-cd]indole-4-carboxylate with a melting point of 185°-188° C.

D) 41.5 g of the product obtained above were dissolved in 1.2 l of tetrahydrofuran. 48.7 g of sodium borohydride were added in portions to the stirred solution at room temperature. Subsequently 780 ml of ethanol were added dropwise and the reaction mixture was heated at 50° C. for 1.5 hours. To work up the reaction mixture it was diluted with dichloromethane, and the organic phase was extracted with water. The aqueous phase was subsequently extracted four times with a 95:5 dichloromethane/methanol mixture. The combined organic phases were dried over sodium sulfate and filtered, and the filtrate was evaporated. The remaining solid residue was dissolved in methanol and crystallized. The crystals were filtered out, washed with a 8:2 methanol/diethyl ether mixture and dried. 31.3 g of 4-hydroxymethyl-3,4,5,6-tetrahydro-6-oxo-1H-azepino[5,4,3-cd]indole were obtained with a melting point of 186° to 187° C.

E) 31.3 g of the product obtained above were dissolved in 190 ml of pyridine. Subsequently 33 g of p-toluenesulfonyl chloride were added to the stirred solution while cooling in ice. The reaction mixture was stirred at room temperature for 24 hours. To work up the reaction mixture it was poured into 300 ml of an ice-cooled, saturated aqueous citric acid solution. The acidic aqueous phase was extracted three times with dichloromethane. The combined organic extracts were dried over sodium sulfate, filtered and evaporated. The remaining residue was dissolved in methanol and crystallized by adding diethyl ether. The crystals were filtered out, washed with a 7:3 methanol/diethyl ether mixture and dried. 36.5 g of 4-(p-toluenesulfonyloxymethyl)-3,4,5,6-tetrahydro-6-oxo-1H-azepino[5,4,3-cd]indole were obtained with a melting point of 175°-178° C.

F) 5 g of the product obtained above were dissolved in 50 ml of dimethylformamide. 5.3 g of sodium azide were added to the solution The stirred reaction mixture was subsequently heated at 100° C. for 2 hours. To work up the reaction mixture it was cooled and evaporated, the residue was dissolved in dichloromethane, and the dichloromethane phase was washed twice with water, dried over sodium sulfate, filtered and evaporated. The remaining oily residue was dissolved in ethyl acetate and crystallized on addition of diethyl ether. The crystals were filtered and dried. 2.8 g of 4-azidomethyl-3,4,5,6-tetrahydro-6-oxo-1H-azepino[5,4,3-cd]indole were obtained with a melting point of 152° to 153° C.

G) 2.8 g of the product obtained above were dissolved in 30 ml of methanol A spatula tip of Raney nickel was added to the solution, then 2 3 ml of hydrazine hydrate were added with stirring, and the reaction mixture was stirred at room temperature for a further 2 hours. For working up, the catalyst was filtered out with suction through asbestos slurry (Theorit ™) and the filtrate was evaporated. The crude title compound which remained as residue was dissolved in methanol and converted into its hydrochloride as described in Example 1C). The resulting crystals were filtered, washed with an 8:2 methanol/diethyl ether mixture and dried. 2.8 g of 4-aminomethyl-3,4,5,6-tetrahydro-6-oxo-1H-azepino[5,4,3-cd]indole hydrochloride were obtained with a melting point of 259° to 265° C.

EXAMPLE 8

4-(2-Aminoethyl)-3,4,5,6-tetrahydro-6-oxo-1H-azepino[5,4,3-cd]indole

A) 5 g of 4-(p-toluenesulfonyloxymethyl)-3,4,5,6-tetrahydro-6-oxo-1H-azepino[5,4,3-cd]indole (see Example 7E for preparation) were dissolved in 25 ml of dimethylformamide. 970 mg of potassium cyanide were added to the solution. The stirred reaction mixture was heated at 65° C. for 3 hours. To work up the reaction mixture it was cooled and then diluted with water and extracted three times with ethyl acetate. The combined organic phases were dried over sodium sulfate, filtered and evaporated. The oily residue was dissolved in methanol, and diethyl ether was added to the solution until crystallisation occurred. The crystals were filtered out with suction, washed with a 8:2 methanol/diethyl ether mixture and dried 2.4 g of 4 -cyanomethyl-3,4,5,6-tetrahydro-6-oxo-1H-azepino[5,4,3-cd]indole were obtained with a melting point of 197° to 198° C.

B) 1.8 g of the product obtained above were dissolved in 250 ml of methanol saturated with ammonia at 0° C. A spatula tip of Raney nickel was added to the solution. The reaction mixture was subsequently transferred into an autoclave and hydrogenated while stirring at 50° C. under a hydrogen pressure of 50 bar for 5 hours To work up, the catalyst was filtered out and the filtrate was evaporated. The remaining residue was purified by low-pressure chromatography on silica gel using methanol/dichloro-methane/diethylamine 17:80:3 as the eluent. The title compound was obtained as an oil.

The title base obtained above was dissolved in methanol and reacted with maleic acid analogously to the method described in Example 3. 1.4 g of 4-(2-aminoethyl)-3,4,5,6-tetrahydro-6-oxo-1H-azepino[5,4,3-cd]indolehydrogenmaleate were obtained with a melting point of 209° to 210° C.

EXAMPLE 9

1-Methyl-3-aminomethyl-3 4 5 6-tetrahydro-6-oxo-1H-azepino[5,4,3-cd]indole

A) 2.1 g of 80% pure sodium hydride were added in portions to a solution of 7 g of methyl 3-formylindole-4-carboxylate (see Example 1A for preparation) in 250 ml of dry dimethylformamide at room temperature under a nitrogen atmosphere. The reaction mixture was stirred at 50° C. for 1 hour. Subsequently, 7 ml of methyl iodide was added through a dropping funnel, and the reaction mixture was stirred at 50° C. for a further 2 hours. To work up the reaction mixture it was evaporated to dryness under reduced pressure and taken up in a mixture of 50 ml of water and 50 ml of dichloromethane. The dichloromethane phase was separated, and the aqueous phase was extracted once more with 50 ml of dichloromethane. The organic phases were combined, dried over sodium sulfate, filtered and evaporated. The remaining crystalline crude product was recrystallized from diethyl ether. Drying of the crystals resulted in 6.9 g of methyl 1-methyl-3-formylindole-4-carboxylate with a melting point of 128°-129° C.

B) 6.9 g of the product obtained above were mixed at room temperature with 70 ml of nitromethane and 1 ml of 1,8-diazabicyclo[5.4.0]undec-7-ene(1.5-5) and the reaction mixture was stirred at a temperature of 65° C. for 4 hours. The reaction mixture was subsequently worked up as described in Example 1B). 5.1 g of methyl 1-methyl-3-(1,3-dinitro-2-propyl)indole-4-carboxylate were obtained with a melting point of 142°-145° C.

C) 5.1 g of the product obtained above were dissolved in 60 ml of methanol and reacted in the presence of a spoon tip of Raney nickel with 10 ml of hydrazine hydrate by the method described in Example 1C). After the reaction was complete, the catalyst was filtered out and the filtrate was evaporated under reduced pressure. The crude title compound which remained as a foam-like residue was dissolved in methanol and converted into its hydrochloride as described in Example 1C). 3.2 g of 1-methyl-3-aminomethyl-3,4,5,6-tetrahydro-6-oxo-1H-azepino[5,4,3-cd]indole hydrochloride were obtained with a melting point of 256°-261° C.

EXAMPLE 10

1-Benzyl-3-aminomethyl-3,4,5,6-tetrahydro-6-oxo-1H-azepino[5,4,3-cd]indole

A) 28 g of methyl 3-formylindole-4-carboxylate (see Example 1A for preparation) were dissolved in 230 ml of nitromethane. 4.2 g of ammonium acetate were added to the solution, and the reaction mixture was boiled under reflux for 1 hour. To work up the reaction mixture it was cooled to room temperature, diluted with 150 ml of a 9:1 ethyl acetate/methanol mixture and subsequently poured into 150 ml of water. The organic phase was separated, dried over sodium sulfate, filtered and concentrated under slightly reduced pressure. The product which crystallized out of the concentrated solution was filtered and dried 25 g of methyl 3-(2-nitrovinyl)indole-4-carboxylate were obtained with a melting point of 187°-190° C.

B) 12 g of the product obtained above were dissolved in 200 ml of dry dimethylformamide. 3 g of sodium hydride were added in portions to the solution at room temperature under a nitrogen atmosphere. The reaction mixture was subsequently heated to 60° C. and 6.3 ml of benzyl bromide were added dropwise through a dropping funnel. The reaction mixture was then heated to 80° C. and stirred at this temperature for 1 hour. To work up the reaction mixture it was evaporated to dryness under reduced pressure, and the residue was taken up in a water/ethyl acetate mixture. The organic phase was separated and concentrated. The remaining residue was purified by column chromatography on silica gel under slightly elevated pressure (flash chromatography) using ethyl acetate as eluent. The residue remaining after concentration of the eluate was crystallized from dichloromethane/diethyl ether 1:9. Drying resulted in 10.8 g of crystalline methyl 1-benzyl-3-(2-nitrovinyl)indole-4-carboxylate, which was immediately processed further.

C) 10.8 g of the product obtained above were dissolved in 150 ml of methanol 33 ml of nitromethane were added to the solution at room temperature, and then 2 ml of diazabicyclo[5.4.0]undec-7-ene(1.5-5) were slowly added. The reaction mixture was subsequently stirred at room temperature for 1 hour. To work up the reaction mixture it was diluted with 150 ml of water and extracted three times with 100 ml portions of dichloromethane. The organic phases were combined, dried over sodium sulfate, filtered and evaporated. The oily crude product which remained as residue was purified by flash chromatography on silica gel using ethyl acetate as eluent. The residue remaining after concentration of the eluate was crystallized from isopropanol-/ethyl acetate 2:8. Drying resulted in 10.3 g of crystalline methyl 1-benzyl-3-(1,3-dinitro-2-propyl)indole-4-carboxylate, which was immediately processed further.

D) 10.3 g of the product obtained above were dissolved in 250 ml of methanol and reacted with 34 ml of hydrazine hydrate in the presence of 3 g of Raney nickel washed with methanol by the method described in Example 1C). The reaction mixture was worked up as described in Example 1C). The title compound was obtained as an oil.

The oily title base obtained above was converted into its hydrochloride by the method described in Example 1C). 7.4 g of 1-benzyl-3-aminomethyl-3,4,5,6-tetrahydro-6-oxo-1H-azepino[5,4,3-cd]indole hydrochloride were obtained with a melting point of 167° to 169° C.

EXAMPLE 11

3-Aminomethyl-5-methyl-3,4,5,6-tetrahydro-6-oxo-1H-azepino[5,4,3-cd]indole

A) 16 g of 3-aminomethyl-3,4,5,6-tetrahydro-6-oxo-1H-azepino[5,4,3-cd]indole hydrate (see Example 1C for preparation) were added in portions over the course of 30 minutes to 50 ml of trifluoroacetic anhydride while stirring and cooling in ice. The reaction mixture was stirred at 20° C. under a nitrogen atmosphere for 2 hours. The reaction mixture was subsequently evaporated to dryness under reduced pressure (water pump vacuum). The residue was dissolved in 200 ml of ethyl acetate. Saturated aqueous sodium bicarbonate solution was added to the solution until a pH of 8.5 was reached. The treatment with the saturated aqueous sodium bicarbonate solution neutralized residues of the trifluoroacetic acid which was formed and excess trifluoroacetic anhydride and, at the same time, eliminated again any trifluoroacetyl radicals attached to the nitrogen atom in position 5 of the ring framework. Subsequently the organic phase was separated, the aqueous phase was extracted twice more with 50 ml portions of ethyl acetate, and the organic phases were combined, dried over sodium sulfate, filtered and evaporated. The remaining residue was crystallized from ethyl acetate with the addition of diethyl ether. Drying resulted in 18 g of 3-trifluoroacetamidomethyl-3,4,5,6-tetrahydro-6-oxo-1H-azepino[5,4,3-cd]indole with a melting point of 228°-232° C.

B) 6 g of the product obtained above were dissolved in 40 ml of formic acid (98 to 100%) at room temperature. 95 ml of acetic anhydride were added dropwise distributed over a period of 8 hours to the solution at a temperature of 55 to 65° C. The reaction mixture was stirred at room temperature for a further 12 hours. The solution was subsequently evaporated under reduced pressure (water pump vacuum) and the residue was taken up in ethyl acetate and worked up as described in Example 11A). 5.3 g of crystalline 3-trifluoroacetamidomethyl-5-formyl-3,4,5,6-tetrahydro-6-oxo-1H-azepino[5,4,3-cd]indole were obtained with a melting point of 198°-205° C.

C) 4 g of the product obtained above were dissolved in 80 ml of absolute tetrahydrofuran, and the solution was cooled to −78° C. under a nitrogen atmosphere. At this temperature 11.8 ml of a 1 molar solution of diisobutylaluminium hydride in toluene were slowly added dropwise. The cooling was then removed. After 2 hours, 80 ml of ethyl acetate and 60 ml of a 10% strength aqueous citric acid solution were added to the solution. The organic phase was separated and the aqueous phase was extracted twice more with 80 ml portions of ethyl acetate. The organic phases were combined, dried over sodium sulfate, filtered and evaporated under reduced pressure (water pump vacuum). The remaining residue was cystallized from ethyl acetate/-diethyl ether. Drying resulted in 3.4 g of 3-trifluoroacetamidomethyl-5-hydroxymethyl-3,4,5,6-tetrahydro-6-oxo-1H-azepino[5,4,3-cd]indole with a melting point of 150°-151.5° C.

D) 25.2 ml of trifluoroacetic acid were added dropwise to a vigorously stirred suspension of 1.08% g of sodium borohydride in 60 ml of tetrahydrofuran while cooling in ice. To this mixture was added dropwise a solution of 1.8 g of the product obtained above in 60 ml of tetrahydrofuran over the course of 30 minutes while cooling in ice. The cooling was then removed, and the reaction mixture was heated at 60° C. for 1 hour. The reaction mixture was subsequently concentrated to 10 ml under water pump vacuum and further processed as described in Example 11A). The resulting oily product was purified by chromatography under moderately elevated pressure (=low-pressure chromatography under 3 to 6 bar) on silica gel using ethyl acetate as eluent The purified product was crystallized from ethyl acetate/diethyl ether. 1.2 g of 3-trifluoroacetamidomethyl-5-methyl-3,4,5,6-tetrahydro-6-oxo-1H-azepino[5,4,3-cd]indole were obtained with a melting point of 174°-177° C.

E) 1.2 g of the product obtained above were dissolved in 40 ml of methanol. 40 ml of a 5% strength aqueous potassium carbonate solution were added to the solution. The reaction mixture was stirred at room temperature for 8 hours. To work up the reaction mixture it was subsequently purified by chromatography under moderately elevated pressure (=low-pressure chromatography under 3 to 6 bar) on silica gel using methanol/25% strength aqueous ammonia solution 97:3 as eluent. The purified product was crystallized from methanol/diethyl ether. 0.82 g of 3-aminomethyl-5-methyl-3,4,5,6-tetrahydro-6-oxo-1H-azepino[5,4,3-cd]indole was obtained with a melting point of 85° to 87° C.

F) The 3-aminomethyl-5-methyl-3,4,5,6-tetrahydro-6-oxo-1H-azepino[5,4,3-cd]indole can also be obtained by debenzylation of 1-benzyl-3-benzylaminomethyl-5-methyl-3,4,5,6-tetrahydro-6-oxo-1H-azepino[5,4,3-cd]indole (see Example 18 for preparation) by hydrogenolysis analogously to the method described in Example 4 but under a hydrogen pressure of 10 bar.

EXAMPLE 12

3-Amino-5-methoxymethyl-3,4,5,6-tetrahydro-6-oxo-1H-azepino[5,4,3-cd]indole 0.1 g of p-toluenesulfonic acid was added to a solution of 1.5 g of 3-trifluoroacetamidomethyl-5-hydroxymethyl-3,4,5,6-tetrahydro-6-oxo-1H-azepino[5,4,3-cd]indole (see Example 11C for preparation) in 25 ml of methanol, and the solution was heated under reflux for 2 hours. The reaction mixture was then concentrated, and saturated aqueous potassium carbonate solution was added to the residue until a pH of 11 was reached, and the mixture was stirred at room temperature for 4 hours. The treatment with the saturated aqueous potassium carbonate solution eliminated the trifluoroacetyl protective group and neutralized the p-toluenesulfonic acid. To work up the reaction mixture it was subsequently evaporated to dryness, the residue was taken up in methanol, insoluble components were removed by filtration, and the residue on the filter was washed twice more with 30 ml portions of methanol. The combined methanol phases were evaporated and the residue was purified by chromatography under moderately elevated pressure (=low-pressure chromatography under 3 to 6 bar) on silica gel using methanol/25% strength aqueous ammonia solution 97:3 as eluent. The title compound which remained after concentration of the eluate was crystallized from ethanol/ether 9:1. 0.5 g of 3-aminomethyl-5-methoxymethyl-3,4,5,6-tetrahydro-6-oxo-1H-azepino[5,4,3-cd]indole was obtained with a melting point of 160° to 163° C.

EXAMPLE 13

3-Aminomethyl-1-(3-phenylpropyl)-3,4,5,6-tetrahydro-6-oxo-1H-azepino[5,4,3-cd]indole 2 g of 3-trifluoroacetamidomethyl-3,4,5,6-tetrahydro-6-oxo-1H-azepino[5,4,3-cd]indole (for preparation see Example 11A) were dissolved in 40 ml of dry dimethylformamide. 0.8 g of sodium hydride was added to the solution, and the reaction mixture was stirred under a nitrogen atmosphere for 1 hour. Subsequently 3.9 ml of 3-phenylpropyl bromide were added dropwise and the reaction mixture was heated under reflux for 6 hours. The reaction mixture was then evaporated under reduced pressure (water pump vacuum) and the oily residue was dissolved in a mixture of 40 ml of ethyl acetate and 40 ml of a 5% strength aqueous citric acid solution. The organic phase was separated, and the aqueous phase was extracted twice more with 30 ml portions of ethyl acetate. The combined organic extracts were dried over sodium sulfate, filtered and concentrated The resulting oily crude 3-trifluoroacetamidomethyl-1-(3-phenylpropyl)-3,4,5,6-tetrahydro-6-oxo-1H-azepino[5,4,3-cd]indole was purified by chromatography under moderately elevated pressure (low-pressure chromatography) on silica gel using cyclohexane/ethyl acetate 1:1 as the eluent. The fractions containing the purified product were combined and concentrated. To eliminate the trifluoroacetyl protective group, the resulting product was dissolved in 40 ml of methanol, and 40 ml of saturated aqueous potassium carbonate solution was added to the solution, which was then stirred at room temperature for 8 hours. Subsequently the reaction mixture was worked up by the method described in Example 11E. The resulting oily title base was dissolved in isopropanol, and ethereal hydrochloric acid solution was added to the solution. 1.0 g of 3-aminomethyl-1-(3-phenylpropyl)-3,4,5,6-tetrahydro-6-oxo-1H-azepino[5,4,3-cd]indole hydrochloride was obtained with a melting point of 118° C.

EXAMPLE 14

3-(1-Piperidinylmethyl)-3,4,5,6-tetrahydro-6-oxo-1H-azepino[5,4,3-cd]indole 4 g of 3-aminomethyl-3,4,5,6-tetrahydro-6-oxo-1H-azepino[5,4,3-Cd]indole hydrate (for preparation see Example 1C) were dissolved in 40 ml of dimethylformamide. 2.6 ml of triethylamine were added to the solution and subsequently, while stirring at room temperature, 2 4 ml of 1,5-dibromopentane were added. The reaction mixture was heated at 50° C. for 3.5 hours. The reaction mixture was worked up by evaporating it under reduced pressure (water pump vacuum) and taking up the residue in a 9:1 dichloromethane/methanol mixture. Then saturated aqueous sodium carbonate solution was added until pH 11 was reached. The organic phase was separated and the aqueous phase was washed twice more with 50 ml portions of the dichloromethane/methanol mixture. The combined organic phases were dried over sodium sulfate, filtered and evaporated. The residue was dissolved in ethanol, and diethyl ether was added to the solution until a slight turbidity appeared. The resulting crystals were filtered out and dried. 3.5 g of crystalline 3-(1-piperidinylmethyl)-3,4,5,6-tetrahydro-6-oxo-1H-azepino[5,4,3-cd]indole were obtained with a melting point of 119° to 122° C.

EXAMPLE 15

3-(Dimethylaminomethylideneaminomethyl)-3,4,5,6-tetrahydro-6-oxo-1H-azepino[5,4,3-cd]indole 2 g of 3-aminomethyl-3,4,5,6-tetrahydro-6-oxo-1H-azepino[5,4,3-cd]indole hydrate (see Example 1C for preparation) were dissolved in 20 ml of dimethylformamide at room temperature. 2.6 ml of dimethylformamide dimethyl acetal were added to the stirred solution. The reaction mixture was stirred at room temperature for 4 hours. The reaction mixture was subsequently concentrated under reduced pressure (water pump vacuum), and the oily residue was dissolved in 50 ml of ethyl acetate. Diethyl ether was added to the solution until a slight turbidity formed. 2.2 g of the crude title base crystallized out.

2.2 g of the crude title base obtained above were dissolved in methanol, and the solution was adjusted to a pH of approximately 1 by adding ethereal hydrochloric acid solution. The solution was then evaporated, and the remaining hydrochloride of the title compound was crystallized from butyl acetate with the addition of isopropanol. Drying of the crystals resulted in 1.3 g of 3-(dimethylaminomethylideneaminomethyl)-3,4,5,6-tetrahydro-6 -oxo-1H-azepino[5,4,3-cd]indole hydrochloride with a melting point of 178° to 179° C.

EXAMPLE 16

3-(Dimethylaminomethylideneaminomethyl)-3,4,5,6-tetrahydro-6-oxo-1H-azepino[5,4,3-cd]indole 1 g of 3-aminomethyl-3,4,5,6-tetrahydro-6-oxo-1H-azepino[5,4,3-cd]indole hydrate (see Example 1C for preparation) was dissolved in 10 ml of dimethylformamide at room temperature. 1 g of N-chloromethylene-N,N-dimethyliminium chloride was added to this solution. The reaction mixture was subsequently stirred at room temperature for 2 hours. To work up the reaction mixture it was evaporated under reduced pressure (water pump vacuum) and the residue was taken up in a mixture of equal parts of water and ethyl acetate. The aqueous phase was adjusted to a pH of 8.5 by adding saturated sodium bicarbonate solution, then the organic phase was separated and the aqueous phase was extracted three times more with 50 ml portions of ethyl acetate. The combined organic extracts were concentrated to 25 ml. The solution of the title compound obtained in this way was further worked up as described in Example 15. 0.5 g of 3-(dimethylaminomethylideneamino-methyl)-3,4,5,6-tetrahydro-6-oxo-1H-azepino[5,4,3-cd]indole hydrochloride was obtained with a melting point of 178° to 179° C.

EXAMPLE 17

4-(4-Phenylpiperazin-1-ylmethyl)-3,4,5,6-tetrahydro-6-oxo-1H-azepino[5,4,3-cd]indole 2.2 g of 4-(p-toluenesulfonyloxymethyl)-3,4,5,6-tetrahydro-6-oxo-1H-azepino[5,4,3-cd]indole (for preparation see Example 7E) were mixed with 9 ml of 1-phenylpiperazine, and the mixture was stirred at a temperature of 80° C. for 4 hours. Subsequent cooling resulted in the crude title compound crystallising out. It was filtered out and washed with a mixture of equal parts of methanol and water. Drying resulted in 1.7 g of 4-(4-phenyl-1-piperazinylmethyl)- 3,4,5,6-tetrahydro-6-oxo-1H-azepino[5,4,3-cd]indole with a melting point of 184° to 185° C.

EXAMPLE 18

1-Benzyl-3-benzylaminomethyl-5-methyl-3,4,5,6-tetrahydro-6-oxo-1H-azepino[5,4,3-cd]indole A) 4 g of oily i-benzyl-3-aminomethyl-3,4,5,6-tetrahydro-6-oxo-1H-azepino(5,4,3-cd]indole (see Example 10 for preparation) were reacted with benzaldehyde by the method described in Example 2, and the resulting Schiff's base was reduced by the method described in Example 2. The reaction mixture was worked up as described in Example 2. 4.3 g of 1-benzyl-3-benzylaminomethyl-3,4,5,6-tetrahydro-6-oxo-1H-azepino[5,4,3-cd]indole were obtained.

B) 4.3 g of the product obtained above were reacted with trifluoroacetic anhydride by the method described in Example 11 A, and the reaction mixture was worked up as described in Example 11 A. 4.1 g of 1-benzyl-3-[N-(benzyl-trifluoroacetamidomethyl]-3,4,5,6-tetrahydro-6-oxo-1H-azepino[5,4,3-cd]indole were obtained as a foam-like product.

C) 4.1 g of the product obtained above were dissolved in 100 ml of absolute tetrahydrofuran. A solution of 1.15 g of potassium tert-butylate in ml of tetrahydrofuran was added dropwise to the solution at a temperature of −20° C. under a nitrogen atmosphere. The reaction mixture was stirred at −20° C. for 1 hour, and subsequently a solution of 0.85 ml of dimethyl sulfate in 5 ml of tetrahydrofuran was added dropwise at this temperature. The reaction mixture was stirred at −20° C. under a nitrogen atmosphere for a further hour. The cooling was subsequently removed. After room temperature was reached, the reaction mixture was concentrated to about 20 ml under reduced pressure (water pump vacuum) and subsequently diluted with 100 ml of water and 50 ml of dichloromethane. Saturated aqueous potassium carbonate solution was then added to the two-phase mixture until a pH of approximately 11 was reached. The mixture was subsequently stirred vigorously so that there was thorough mixing of the two phases for 4 hours, during which the trifluoroacetyl protective group was also eliminated by hydrolysis. Subsequently the organic phase was separated, and the aqueous phase was extracted twice more with 50 ml portions of dichloromethane. The combined organic phases were dried over sodium sulfate, filtered and evaporated. The remaining crude product was purified by chromatography on silica gel under slightly elevated pressure (flash chromatography) using ethyl acetate/cyclohexane 7:3 as eluent. 2.I g of 1-benzyl-3-benzylaminomethyl-5-methyl-3,4,5,6-tetrahydro-6-oxo-1H-azepino[5,4,3-cd]indole were obtained as a foam-like product.

EXAMPLE 19

3-[N-(4-Hydroxybenzyl)aminomethyl]-3,4,5,6-tetrahydro-6-oxo-1H-azepino[5,4,3-cd]indole 2 ml of trimethylsilyl iodide were added to a mixture of 1.5 g of 3-[N-(4-methoxybenzyl)aminomethyl]-3,4,5,6-tetrahydro-6-oxo-1H-azepino[5,4,3-cd]indole (see Example 21 for preparation) and 2.5 g of 1,4-diazabicyclo[2.2.2]octane (=DABCO). The reaction mixture was heated at 150° C. under a nitrogen atmosphere for 24 hours. The reaction mixture was cooled to room temperature and then diluted with 25 ml of methanol and acidified with 20% strength aqueous hydrochloric acid. The mixture was then vigorously stirred at room temperature for 2 hours. To work up the reaction mixture it was diluted with 30 ml of water, the aqueous phase was separated and the organic phase was washed twice more with 20 ml portions of water. The combined aqueous phases were neutralized with dilute sodium hydroxide solution and subsequently evaporated under reduced pressure (water pump vacuum). The crude product which remained as an oily residue was purified by chromatography on silica gel under slightly elevated pressure (flash chromatography) using methanol/25% strength aqueous ammonia solution 98:2 as eluent. 0.6 g of 3-[N-(4-hydroxybenzyl)aminomethyl] 3,4,5,6-tetrahydro-6-oxo-1H-azepino(5,4,3-cd]indole was obtained as an oil.

0.6 g of the title base obtained above was dissolved in 20 ml of methanol, and 0.27 g of tartaric acid was added to the solution. Evaporation of this mixture resulted in 0.87 g of amorphous 3-[N-(4-hydroxybenzyl)aminomethyl]-3,4,5,6-tetrahydro-6-oxo-1H-azepino[5,4,3-cd]indole hydrogen tartrate.

EXAMPLE 20

4-Aminomethyl-3,4,5,6-tetrahydro-6-oxo-1H-azepino[5,4,3-cd]indole

A) 2.5 g of 4-(p-toluenesulfonyloxymethyl)-3,4,5,6-tetrahydro-6-oxo-1H-azepino[5,4,3-cd]indole were dissolved in 40 ml of methanol 1.4 g of potassium phthalimide were added to the solution. The reaction mixture was heated under reflux for 6 hours. To work up the reaction mixture it was subsequently evaporated to dryness under reduced pressure (water pump vacuum). The remaining solid residue was dissolved in a 1:1 mixture of dichloromethane and water. The organic phase was separated, and the aqueous phase was washed three more times with 50 ml portions of dichloromethane. The combined organic extracts were dried over sodium sulfate, filtered and evaporated. 1.9 g of 4-(N-phthalimidomethyl)-3,4,5,6-tetrahydro-6-oxo-1H-azepino[5,4,3-cd]indole were obtained and were immediately processed in the next reaction stage.

B) 1.9 g of the product obtained above were dissolved in 50 ml of ethanol 1 ml of hydrazine hydrate was added to the solution. The reaction mixture was heated under reflux for 4 hours. For working up, it was cooled to room temperature, and phthalhydrazide which was formed was filtered out and washed twice with 20 ml portions of ethanol. The filtrate and the washing solutions were combined and evaporated. The remaining crude title compound was purified by chromatography under moderately elevated pressure (=low-pressure chromatography=LPLC under 3 to 6 bar) on silica gel using methanol/aqueous ammonia solution 98:2 as eluent. The title base obtained in this way was converted into its hydrochloride by the method described in Example 7G. 0.7 g of 4-aminomethyl-3,4,5,6-tetrahydro-6-oxo-1H-azepino[5,4,3-cd]indole hydrochloride was obtained with a melting point of 256° to 260° C.

The compounds of formula I listed in the following Table 1 can also be prepared by the processes described in the foregoing examples.

TABLE 1

| Example | R¹ | R² | R³ | Pos* | n | D | R⁴ | R⁶ | Salt Form | M.P. in °C. |
|---|---|---|---|---|---|---|---|---|---|---|
| 21 | H | H | H | 3 | 1 | bi | 4-CH₃O—Ph—CH₂— | H | HCl | 213-234 |
| 22 | H | H | H | 3 | 1 | bi | 3,4-di-CH₃O—Ph—CH₂— | H | HCl | 164-166 |
| 23 | H | H | H | 3 | 1 | bi | 4-Cl—Ph—CH₂— | H | HCl | 200-203 |
| 24 | H | H | H | 3 | 1 | bi | 4-CH₃—Ph—CH₂— | H | HCl | 171-173 |
| 25 | H | H | H | 4 | 1 | bi | —CH₂—CH₂—N(CH₃)—CH₂—CH₂— | | B | 195-196 |
| 26 | H | H | H | 4 | 1 | bi | CH₃— | CH₃— | B | 253-256 |
| 27 | H | H | H | 4 | 1 | bi | 3,4-di-CH₃O—Ph—(CH₂)₂— | CH₃— | B | 163-165 |
| 28 | H | H | H | 4 | 1 | bi | cyclohex- | H | B | 200-203 |
| 29 | H | H | H | 4 | 1 | bi | —CH₂—CH₂—O—CH₂—CH₂— | | HCl | 250-263 |
| 30 | H | H | H | 4 | 1 | bi | —(CH₂)₆— | | HCl | 298-300 |
| 31 | H | H | H | 4 | 1 | bi | (CH₃)₃C— | H | B | 230 |
| 32 | H | H | H | 3 | 1 | bi | 3,4-di-CH₃O—Ph—(CH₂)₂— | H | B | 178-180 |
| 33 | H | H | H | 3 | 1 | bi | 3,4-di-CH₃O—Ph—(CH₂)₂— | C₂H₆— | B | 179-181 |
| 34 | (CH₃)₂—CH— | H | H | 3 | 1 | bi | H | H | HCl | 172-175 |
| 35 | H | H | H | 3 | 1 | bi | 3,4-di-CH₃O—Ph—(CH₂)₂— | 3,4-di-CH₃O—Ph—(CH₂)₂— | B | 159-160 |
| 36 | 3,4-di-CH₃O—Ph—(CH₂)₂— | H | H | 3 | 1 | bi | H | H | HCl | 143-144 |
| 37 | H | H | H | 3 | 1 | bi | —(CH₂)₄— | | HBr | 281-284 |
| 38 | H | H | H | 3 | 1 | bi | n-C₃H₇— | H | B | 82-84 |
| 39 | H | H | H | 3 | 1 | bi | CH₃— | CH₃— | HCl | 253-257 |
| 40 | H | H | H | 3 | 1 | bi | n-C₃H₇— | n-C₃H₇— | B | 113-115 |
| 41 | H | H | H | 3 | 1 | bi | n-C₄H₉— | H | HCl | 153-156 |
| 42 | H | H | H | 3 | 1 | bi | 3,4-di-CH₃O—Ph—(CH₂)₂— | CH₃— | B | 162-163 |
| 43 | H | H | H | 3 | 1 | bi | Ph—CH₂— | C₂H₆— | Hta | 125-127 |
| 44 | H | H | H | 3 | 1 | bi | n-C₆H₁₁— | n-C₆H₁₁— | Hta | 144-147 |
| 45 | H | H | H | 4 | 1 | bi | cycloprop- | H | B | 205-207 |
| 46 | H | H | H | 3 | 1 | bi | n-C₄H₉— | n-C₄H₉— | Hta | 130-133 |
| 47 | H | H | H | 3 | 1 | bi | cycloprop-CH₂— | H | B | 97-100 |
| 48 | H | H | 7-Cl | 3 | 1 | bi | H | H | HCl | 230(D) |
| 49 | H | H | 7-Cl | 3 | 1 | bi | CH₃— | H | HCl | 179(D) |
| 50 | H | CH₃ | H | 3 | 1 | bi | CH₃— | H | HCl | 150(D) |

Pos = position of the side chain on the ring framework, HCl = hydrochloride, B = base, HBr = hydrobromide, Hta = Hydrogen tartrate, b = bond, Ph = phenyl, cycloprop = cyclopropyl, cyclohex = cyclohexyl, d = decomposition

EXAMPLE I

Tablets containing 3-aminomethyl-3,4,5,6-tetrahydro-6-oxo-1H-azepino[5,4,3-cd]indole Tablets having the following composition per tablet were prepared:

| | |
|---|---|
| 3-Aminomethyl-3,4,5,6-tetrahydro-6-oxo-1H-azepino[5,4,3-cd]indole hydrochloride | 20 mg |
| Maize starch | 60 mg |
| Lactose | 135 mg |
| Gelatin (10% strength solution) | 6 mg |

The active compound, the maize starch and the lactose were converted into a paste with the 10% strength gelatin solution. The paste was comminuted and the resulting granules were placed on a suitable metal sheet and dried at 45° C. The dried granules were passed through a comminuting machine and mixed with the following additional adjuvants in a mixer:

| | |
|---|---|
| Talc | 5 mg |
| Magnesium stearate | 5 mg |
| Maize starch | 9 mg | and then compressed to 240 mg tablets.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A compound corresponding to the formula I

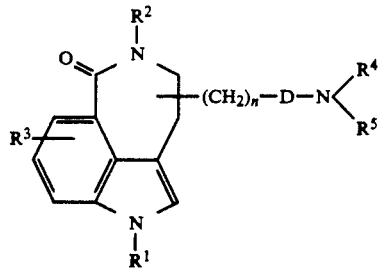

wherein
R¹ represents hydrogen, a lower alkyl or cycloalkyl-alkyl group or a phenyl-lower alkyl group which can optionally be mono- or disubstituted in the phenyl ring by lower alkoxy, hydroxyl, halogen or lower alkyl, R² represents hydrogen or a lower alkyl group optionally substituted in the α-position to the nitrogen atom by lower alkoxy, R³ is hydrogen, lower alkyl, lower alkoxy, halogen, or if R¹, R², R⁴ and R⁵ are free of lower alkoxy groups, R³ may also be hydroxyl, n represents 1, or if the —(CH₂)ₙ— chain is in the 4-position of the ring structure, n may also represent 2;

R⁴ is hydrogen, alkyl having 1 to 5 carbon atoms, cycloalkyl having 3 to 6 carbon atoms, cycloalkylalkyl having 4 to 9 carbon atoms or a phenyl-lower alkyl group optionally mono- or disubstituted in the phenyl ring by lower alkyl, lower alkoxy, hydroxyl or halogen, and R⁵ is hydrogen, alkyl having 1 to 5 carbon atoms, cycloalkyl having 3 to 6 carbon atoms, cycloalkylalkyl having 4 to 9 carbon atoms or a phenyl-lower alkyl group optionally mono- or disubstituted in the phenyl ring by lower alkyl, lower alkoxy, hydroxyl or halogen, or R⁴ and R⁵, together with the nitrogen atom to which they are bonded, form a heterocycle corresponding to the formula

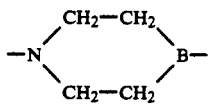

wherein B represents a bond, the methylene group, oxygen, or an imino group —NR⁶—, in which R⁶ is hydrogen, lower alkyl or phenyl or benzyl optionally substituted in the phenyl ring by lower alkyl, lower alkoxy, hydroxyl or halogen, and D represents a bond, or if R⁴ and R⁵ are other than hydrogen, D may also represent the —N=CH— group, or their physiologically acceptable acid addition salts.

2. A compound according to claim 1, wherein R¹ is hydrogen.

3. A compound according to claim 1, wherein R² is hydrogen.

4. A compound according to claim wherein R⁴ is hydrogen, lower alkyl or optionally substituted benzyl and R⁵ is hydrogen.

5. A compound according to claim 1, wherein D represents a bond.

6. A compound according to claim 1, wherein said compound contains a —CH₂—D—NR⁴R⁵ group in the 3-position of the ring structure.

7. A pharmaceutical composition comprising an effective gastric motility-promoting or anti-migraine amount of a compound according to claim 1, and at least one pharmaceutical carrier or adjuvant.

8. A compound corresponding to the formula VII

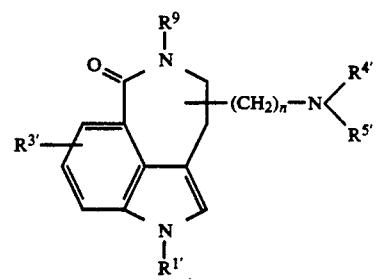

wherein

R¹' represents hydrogen, a lower alkyl or cycloalkylalkyl group or a phenyl-lower alkyl group which can be optionally mono- or disubstituted in the phenyl ring by lower alkoxy, hydroxyl, halogen or lower alkyl, or an amino-protective group, R³' is hydrogen, lower alkyl, lower alkoxy or halogen, n represents 1 or, if the —(CH₂)ₙ— chain is in the 4-position of the ring structure, n may also represent 2;

R⁴' is hydrogen, alkyl having 1 to 5 carbon atoms, cycloalkyl having 3 to 6 carbon atoms, cycloalkylalkyl having 4 to 9 carbon atoms or a phenyl-lower alkyl group which is optionally mono- or disubstituted in the phenyl ring by lower alkyl, lower alkoxy, hydroxyl or halogen, and R⁵' is hydrogen, alkyl having 1 to 5 carbon atoms, cycloalkyl having 3 to 6 carbon atoms, cycloalkylalkyl having 4 to 9 carbon atoms or a phenyl-lower alkyl group which is optionally mono- or disubstituted in the phenyl ring by lower alkyl, lower alkoxy, hydroxyl or halogen, or R⁴' and R⁵', together with the nitrogen atom to which they are bonded, form a heterocycle corresponding to the general formula

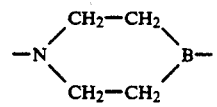

in which B represents a bond, a methylene group, oxygen, or an imino group —NR⁶—, in which R⁶ is hydrogen, lower alkyl or phenyl or benzyl optionally substituted in the phenyl ring by lower alkyl, lower alkoxy, hydroxyl or halogen, but where an NR⁴'R⁵' group in which at least one of R⁴' and R⁵' is hydrogen is protected by a removable amino-protective group, and R⁹ represents a lower 1-hydroxyalkyl group.

* * * * *